(12) United States Patent
Dillin et al.

(10) Patent No.: US 8,653,080 B2
(45) Date of Patent: Feb. 18, 2014

(54) METHODS FOR SCREENING AND COMPOUNDS THAT PROTECT AGAINST AMYLOID DISEASES

(75) Inventors: Andrew Dillin, San Diego, CA (US); Thomas J. Baiga, San Marcos, CA (US); Erik Kapernick, Encinitas, CA (US); Joseph P. Noel, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 711 days.

(21) Appl. No.: 12/687,455

(22) Filed: Jan. 14, 2010

(65) Prior Publication Data

US 2010/0263062 A1    Oct. 14, 2010

Related U.S. Application Data

(60) Provisional application No. 61/144,505, filed on Jan. 14, 2009.

(51) Int. Cl.
| | |
|---|---|
| *A61K 31/497* | (2006.01) |
| *C07D 295/03* | (2006.01) |
| *C07D 401/06* | (2006.01) |
| *C07D 401/10* | (2006.01) |

(52) U.S. Cl.
USPC ............... 514/253.01; 514/255.01; 544/360; 544/383

(58) Field of Classification Search
USPC ............... 514/253.01, 255.01; 544/383, 360
See application file for complete search history.

(56) References Cited

U.S. PATENT DOCUMENTS

| | | | |
|---|---|---|---|
| 5,405,857 A | 4/1995 | Karup et al. | |
| 5,442,064 A | 8/1995 | Pieper et al. | |
| 5,885,997 A | 3/1999 | Lohray et al. | |
| 5,985,884 A | 11/1999 | Lohray et al. | |
| 6,204,265 B1 | 3/2001 | Reichard et al. | |
| 6,235,755 B1 | 5/2001 | El Tayer et al. | |
| 6,310,069 B1 | 10/2001 | Lohray et al. | |
| 6,403,582 B2 | 6/2002 | Reichard et al. | |
| 6,423,723 B1 | 7/2002 | Tayer et al. | |
| 6,492,553 B1 | 12/2002 | Hulme et al. | |
| 6,534,502 B2 | 3/2003 | Reichard et al. | |
| 6,653,338 B2 | 11/2003 | El Tayer et al. | |
| 7,300,939 B2 | 11/2007 | Kuehnert et al. | |
| 7,732,605 B2 | 6/2010 | Hayashi | |
| 2003/0207814 A1 | 11/2003 | Boyce et al. | |
| 2005/0124597 A1 | 6/2005 | Boyce et al. | |
| 2006/0235226 A1 | 10/2006 | Hayashi | |
| 2007/0155730 A1 | 7/2007 | Leit et al. | |

FOREIGN PATENT DOCUMENTS

| | | |
|---|---|---|
| CA | 2 318 351 | 7/1999 |
| WO | WO 92/13847 | 8/1992 |
| WO | WO 99/33805 | 7/1999 |
| WO | WO 99/38844 | 8/1999 |
| WO | WO 00/08015 | 2/2000 |
| WO | WO 00/39114 | 7/2000 |
| WO | WO 01/10799 | 2/2001 |
| WO | WO 03/066587 | 8/2003 |
| WO | WO 2006/002981 | 1/2006 |
| WO | WO 2006/105051 | 10/2006 |
| WO | WO 2007/022638 | 3/2007 |
| WO | WO 2007/062664 | 6/2007 |
| WO | WO 2007/117180 | 10/2007 |
| WO | WO 2008/014613 | 2/2008 |
| WO | WO 2008/112014 A1 | 9/2008 |
| WO | WO 2008/116107 | 9/2008 |
| WO | WO 2008/116815 | 10/2008 |
| WO | WO 2008/128942 | 10/2008 |
| WO | WO 2008/128953 | 10/2008 |
| WO | WO 2008/141074 | 11/2008 |

OTHER PUBLICATIONS

Hulme et al., "Novel Applications of ethyl glyoxalate with the Ugi MCR", Tetrahedron Letters, 40(29), 5295-5299 (1999).

*Primary Examiner* — James O Wilson
*Assistant Examiner* — Ebenezer O Sackey
(74) *Attorney, Agent, or Firm* — Klarquist Sparkman, LLP

(57) ABSTRACT

The disclosure provides methods and compositions useful for screening inhibitors of aggregation mediated proteotoxicity. The disclosure provides transgenic animals and cell useful for such screening. Also provided are compounds useful for inhibiting aggregation mediated proteotoxicity in a subject.

15 Claims, 21 Drawing Sheets

METHODS FOR SCREENING AND COMPOUNDS THAT PROTECT AGAINST AMYLOID DISEASES

CROSS REFERENCE TO RELATED APPLICATIONS

This application claims priority to U.S. Provisional Application No. 61/144,505, filed Jan. 14, 2009, the disclosure of which is incorporated herein by reference in its entirety.

FIELD OF THE DISCLOSURE

The disclosure relates to methods of inhibiting aggregation-mediated proteotoxicity, methods of inhibiting the onset of symptoms of an amyloid disease and methods of identifying compounds that inhibit aggregation-mediated proteotoxicity.

BACKGROUND

It has been known for decades that more than a dozen unrelated proteins can undergo aberrant assembly in vivo to form filaments or fibrils, which are generally referred to as amyloid (for reviews, see Sacchettini and Kelly, Nature Rev. 1:267-75, 2002; Stefani and Dobson, J. Mol. Med. 81:678-99, 2003; Lansbury and Lashuel, Nature 443:774-79, 2006). The presence of extracellular or intracellular aggregates of a specific polypeptide molecule is a hallmark of the recognized amyloid diseases; such aggregates promoting aggregation-mediated proteotoxicity. The polypeptides involved include full-length proteins (e.g., lysozyme and immunoglobulin light chains), peptides (e.g., amylin and atrial natriuretic factor) and fragments of larger proteins produced as a result of normal or abnormal endoproteolytic processing (e.g., Alzheimer's β-amyloid peptide). Abnormal processing is often the result of misfolding (Golde et al., Science 255:728-30, 1992; Shoji et al., Science 258:126-29, 1992; Kimberly et al., J. Biol. Chem. 275:3173-78, 2000). Nearly all full-length amyloidogenic proteins are secreted, suggesting that these proteins misfold after export (Kelly, Structure 5:595-600, 1997; Moyer and Balch, Emerging Therap. Targets 5:165-76, 2001). In some cases the proteins involved have wild-type sequences, as in sporadic forms of the diseases, but in other cases these are variants resulting from genetic mutations associated with familial forms of the diseases.

The presence of misfolded or aggregated proteins triggers a complex biological response, leading to the expression, among others, of the genes for heat shock proteins (Hsp, or molecular chaperone proteins) and proteins involved in the ubiquitin-proteasome pathway (Sherman and Goldberg, Neuron 29: 15-32, 2001). The evolution of such complex biochemical machinery makes clear the fact that it is necessary for cells to isolate and rapidly and efficiently clear any unfolded or misfolded protein as soon as it appears. Until recently, the main amyloid diseases were thought to be restricted to Alzheimer's disease (AD), Parkinson's disease (PD), reactive amyloidosis and the systemic amyloidoses (e.g., immunoglobulin-light-chain-, transthyretin- and gelsolin-based diseases) (Westermark et al, Proc. Natl. Acad. Sci. USA 87:2843-45, 1990; Hurle et al., Proc. Natl. Acad. Sci. USA 91:5446-50, 1994; Selkoe, Science 275:630-31, 1997; Kiuru, Amyloid 5:55-66, 1998). However, amyloid-like disorders are likely far more widespread than previously thought, and could include many common neurodegenerative and neuromuscular pathologies, as well as prion disease. The most intensely studied amyloid disease is AD, where characteristic brain plaques contain β-amyloid. The primary biochemical component of β-amyloid is a 39- to 43-amino acid peptide derived from the β-amyloid precursor protein (APP) through endoproteolysis (Glenner and Wong, Biochem. Biophys. Res. Commun. 83:885-90, 1984).

The deposition of proteins in the form of amyloid fibrils and plaques is the characteristic feature of more than twenty degenerative conditions affecting either the central nervous system or a variety of peripheral tissues.

SUMMARY

Compositions and methods for inhibiting protein aggregation and aggregation-mediated proteotoxicity in a subject are provided. A compound useful in the generation of therapeutic compositions has a general formula I:

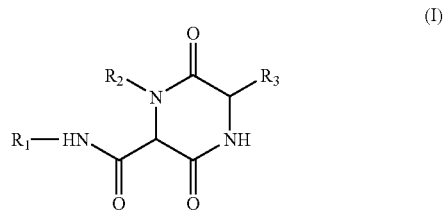

(I)

wherein $R_1$ is aryl, heteroaryl, arylalkyl, or heteroarylalkyl, each optionally substituted; $R_2$ is alkyl, substituted alkyl, aryl, substituted aryl, heteroaryl or substituted heteroaryl; $R_3$ has a formula selected from the group consisting of —$R_4$—X—$R_5$ and —C(R)$_2$—C(R)$_2$—C(R)$_2$—$R_6$; $R_4$ is a bond, alkyl, substituted alkyl, aryl or substituted aryl; $R_5$ is H, alkyl, substituted alkyl, aryl, and substituted aryl; X is selected from the group consisting of O, S, N(R), C(O), C(O)NR, S(O)$_n$, wherein n is 0, 1 or 2; $R_6$ is selected from the group consisting of aryl, optionally substituted aryl, heteroaryl, and substituted heteroaryl; and each R is independently selected from the group consisting of H, aryl, substituted aryl, alkyl, or substituted alkyl; or a salt of any of the foregoing compounds. In one embodiment, $R_1$ is arylalkyl or substituted arylalkyl. In another embodiment, $R_1$ is phenylmethyl or substituted phenylmethyl. In a further embodiment, $R_2$ is alkyl or substituted alkyl. In yet another embodiment, $R_2$ is selected from the group consisting of arylalkyl, substituted arylalkyl, heteroarylalkyl and substituted heteroarylalkyl. In yet another embodiment, $R_2$ is phenylmethyl or substituted phenylmethyl. In yet a further embodiment, $R_2$ is pyridylmethyl or substituted pyridylmethyl. In one embodiment, $R_2$ is alkyl substituted with heterocycle, wherein said alkyl and heterocycle are each optionally substituted. In another embodiment, X is O. In yet another embodiment, $R_5$ is an alcohol protecting group. In yet a further embodiment, $R_5$ is selected from the group consisting of acetyl (Ac), benzoyl (Bz), benzyl (Bn), β-methoxyethoxymethyl ether (MEM), dimethoxytrityl[bis-(4-methoxyphenyl)phenylmethyl, DMT], methoxymethyl ether (MOM), methoxytrityl[(4-methoxyphenyl)diphenylmethyl, MMT), p-methoxybenzyl ether (PMB), methylthiomethyl ether, pivaloyl (Piv), tetrahydropyranyl (THP), trityl (triphenylmethyl, Tr), silyl ether (e.g., trimethylsilyl (TMS), tert-butyldimethylsilyl (TBDMS), tert-butyldimethylsilyloxymethyl (TOM), and triisopropylsilyl (TIPS) ethers), a methyl ethers and ethoxyethyl ethers (EE).

In yet another embodiment, the disclosure provides a compound of Formula II:

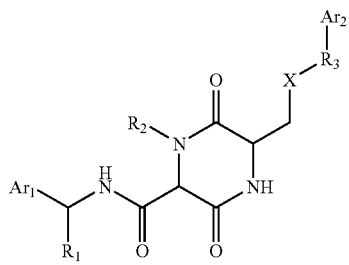

(II)

wherein Ar₁ is an aryl, heteroaryl, a phenyl or substituted phenyl group, wherein R₁ is H, —CH₃, or SO₂R, wherein R is H, aryl, substituted aryl, alkyl, or substituted alkyl; wherein R₂ is any alkyl, aryl, heteroaryl; wherein X is O, S, or NH, wherein R₃ is (CH₂)ₙ, and n is 0-3 when X=O or S or R₃=C=O where X is NH; wherein Ar₂ is any aryl or heteroaryl and any salts of any of the foregoing.

The disclosure also provides compounds of formula I or II that include, but are not limited to:

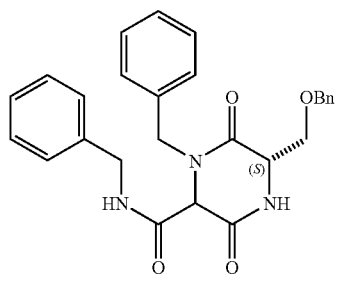

A7

Mol. Wt.: 457.52
CLogP: 3.94845

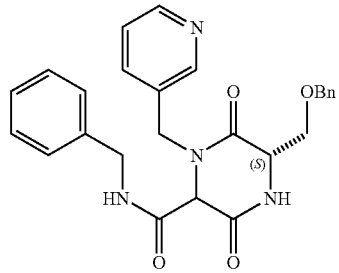

E7

Mol. Wt.: 458.51
CLogP: 2.45145

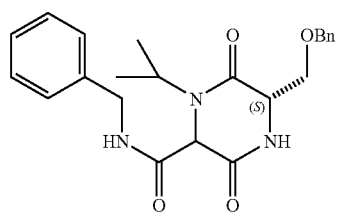

B7

Mol. Wt.: 409.48
CLogP: 3.2295

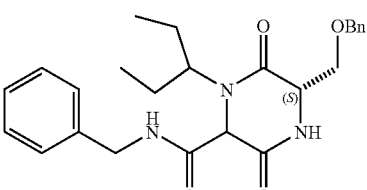

F7

Mol. Wt.: 437.53
CLogP: 4.2875

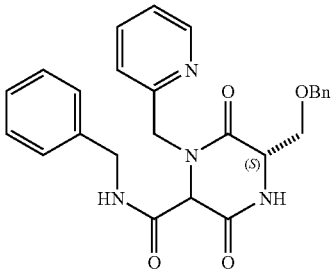

C7

Mol. Wt.: 458.51
CLogP: 2.45145

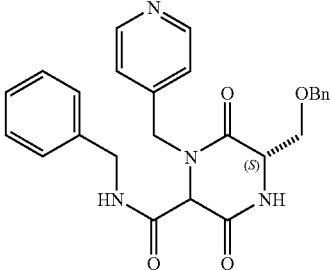

G7

Mol. Wt.: 458.51
CLogP: 2.45145

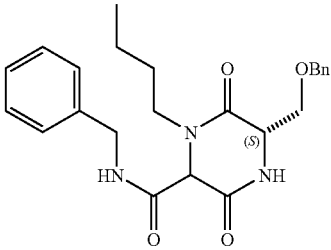

D7

Mol. Wt.: 423.5
CLogP: 3.9785

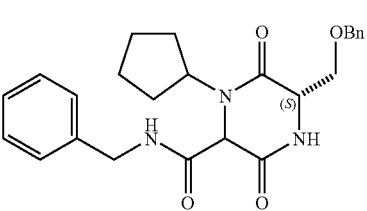

H7

Mol. Wt.: 435.52
CLogP: 3.74545

The disclosure also provides compositions comprising a compound of formula I or II including A7-H7, or derivatives thereof. Such compositions include a compound of the disclosure and pharmaceutically acceptable carriers and may further include other active compounds. The compositions can be used in conjunction with other compounds known to inhibit protein aggregation to enhance their activities. The compositions are provided in therapeutically effective amounts to a subject in need thereof to inhibit protein aggregation. The compositions find use in treating and preventing amyloid diseases, such as neurodegenerative diseases, associated with protein aggregation and aggregation-mediated proteotoxicity.

Also provided are methods for identifying compounds that inhibit protein aggregation. The methods include the expression of a β-amyloid peptide in a non-human transgenic animal and determining the effect of a test compound on paralysis and/or protein aggregation. In one embodiment, an assay utilizing a C. elegans modified to express a β-amyloid peptide is utilized. In another embodiment, protein aggregation is measured by a fluorescent indicator such as a green fluorescent protein (GFP). In one embodiment, a method of identifying a compound that inhibits aggregation-mediated proteotoxicity in a subject, includes: (1) providing a first C. elegans expressing a β-amyloid peptide; (2) determining the amount of fluorescence in the first C. elegans; (3) exposing a second C. elegans expressing the β-amyloid peptide to a test compound; (4) determining the fluorescence in the second C. elegans; and (5) comparing the levels of fluorescence in the first and second C. elegans, where the test compound is identified as a compound that inhibits aggregation-mediated proteotoxicity in a subject when the level of fluorescence in the second C. elegans is less than the level of fluorescence in the first C. elegans. In a non-limiting example, the β-amyloid peptide is expressed in body wall muscles.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 6 and 7 show two graphs depicting the effect of agents A7-H7 on fluorescence (% vGFP) over time (hours) in the C. elegans model described in the Example. Also shown are the effects of combinations of agents at half concentrations each. FIGS. 8 and 9 show two graphs of dose-timing effect of the agents D7 and F7; D7H and F7H, the agent was given for life of the worm; D7Hup and F7Hup, agent give at upshift; and D7Ht0 and F7Ht0, agent given at 0 time.

DETAILED DESCRIPTION

Figure 1:
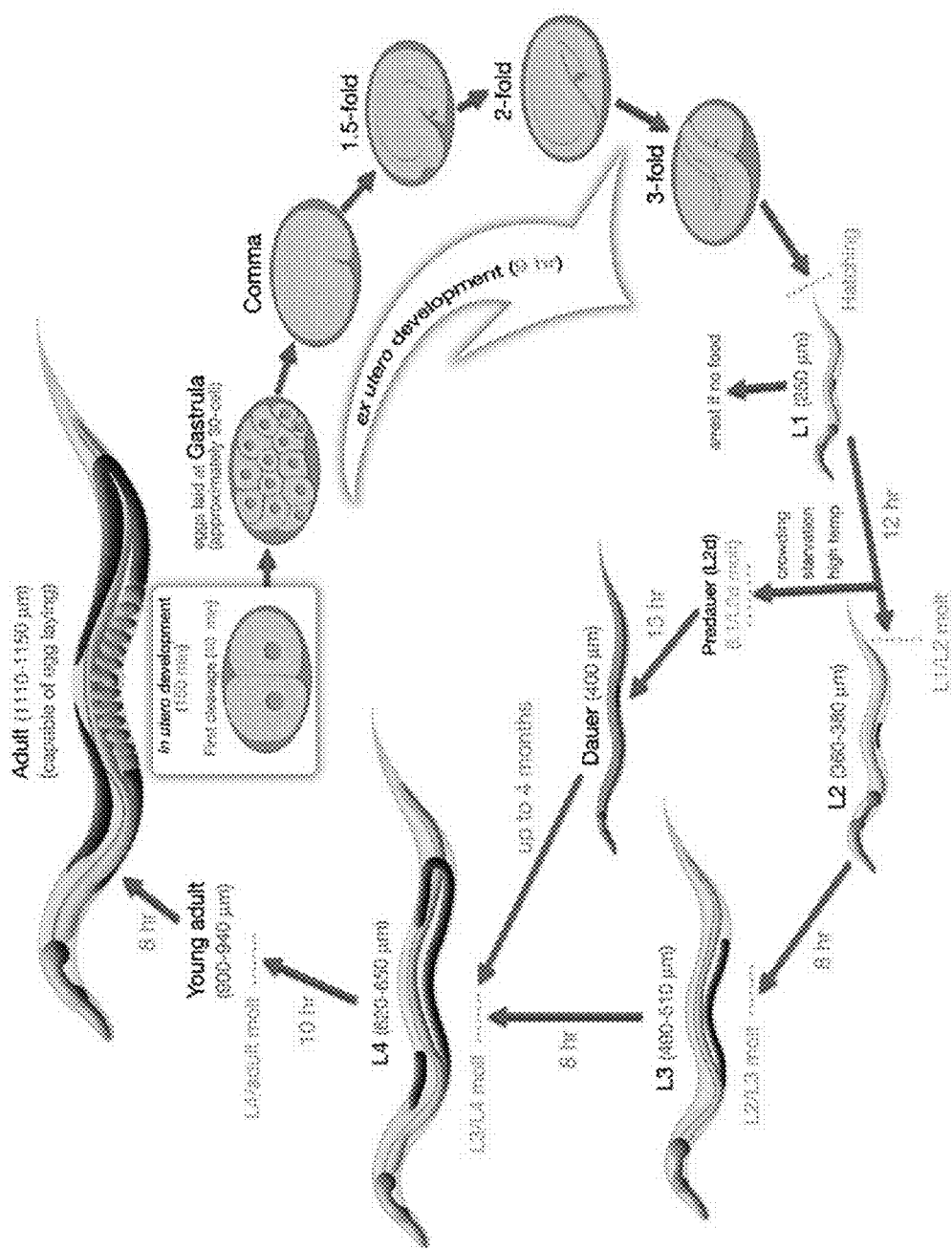
FIG. 1 show the life cycle of a C. elegans. Reproduced from http://www.wormatlas.org/hermaphrodite/introduction/IMAGES/introfig6.jpg.

As used herein and in the appended claims, the singular forms "a," "and," and "the" include plural referents unless the context clearly dictates otherwise. Thus, for example, reference to "a protein" includes a plurality of such proteins and reference to "the compound" includes reference to one or more compounds and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Compositions and methods for inhibiting protein aggregation and aggregation-mediated proteotoxicity in a subject are provided. The compositions can be used in conjunction with other compounds known to inhibit protein aggregation and to enhance their activities. The compositions are provided in therapeutically effective amounts to a subject in need thereof to inhibit protein aggregation. The compositions find use in treating and preventing neurodegenerative diseases associated with protein aggregation and aggregation-mediated proteotoxicity.

An amyloid disease (or amyloidosis) is any of a group of disparate conditions of diverse etiologies characterized by the accumulation of amyloid in various organs and tissues of the body, with accompanying impairment of vital function. Amyloid is the generic term for a group of diverse but specific protein deposits which are seen in a number of different diseases. Amyloid deposits are metabolically inert but interfere physically with organ structure and function. Though diverse in their occurrence, all amyloid deposits have common morphologic properties, stain with specific dyes (e.g., Congo red) and have a characteristic red-green birefringent appearance in polarized light after staining. They also share common ultrastructural features and common X-ray diffraction and infrared spectra. The associated disease states may be inflammatory, hereditary or neoplastic, and the deposition can be local, generalized or systemic. There are three major systemic forms of amyloidosis: primary, secondary and familial. In addition, there are two major localized forms, β-amyloid peptide (Aβ) and islet amyloid polypeptide (IAPP, which occurs in the pancreas of type-2 diabetes subjects), as well as several miscellaneous forms (e.g., Aβ2-microglobulin associated with chronic hemodialysis).

Primary amyloidosis (AL) is a monoclonal plasma cell disorder in which the abnormal protein is an immunoglobulin, usually a light chain fragment (i.e., Bence Jones protein) but occasionally a heavy chain fragment (AH amyloidosis). These chains either have an aberrant structure or are processed abnormally, resulting in the formation of insoluble deposits. Common sites for deposition include the skin, nerves, heart, gastrointestinal tract (including tongue), kidney, liver, spleen, and blood vessels. Mild plasmacytosis occurs in the bone marrow, suggestive of multiple myeloma, but most AL subjects do not have true multiple myeloma (however, about 10-20% of subjects with multiple myeloma also develop AL amyloidosis). Secondary amyloidosis (AA) can occur secondary to several infectious, inflammatory and malignant (e.g., myeloma) conditions and is caused by the degradation of the acute-phase reactant serum amyloid A (SAA) protein. Common causative infections include tuberculosis (TB), bronchiectasis, osteomyelitis, and leprosy. Inflammatory conditions include rheumatoid arthritis (RA), juvenile RA, Crohn's disease, and familial Mediterranean fever. Inflammatory cytokines (e.g., IL-1, tumor necrosis factor and IL-6) that are produced in these disorders cause increased hepatic production of the precursor protein SAA, which circulates in the serum. AA amyloidosis shows a predilection for the spleen, liver, kidneys, adrenals, and lymph nodes, but involvement of the heart and peripheral or autonomic nerves is also known. Familial amyloidosis results from accumulation of a normal or mutated version of a plasma protein (e.g., transthyretin (TTR) in familial amyloid polyneuropathy I or senile systemic amyloidosis). Nearly all of the abnormal protein is produced by the liver, and over 80 mutations of the gene for TTR have been identified, all inherited in an autosomal dominant pattern. Other rare hereditary amyloidoses result from mutations of other physiologic proteins, including apolipoprotein A-I (familial amyloid polyneuropathy III), lysozyme (familial non-neuropathic amyloidosis), fibrinogen (hereditary renal amyloidosis), gelsolin (Finnish hereditary systemic amyloidosis), superoxide dismutase (familial amyotrophic lateral sclerosis), and cystatin C (hereditary cerebral amyloid angiopathy); these amyloidoses have various systemic and localized effects.

Localized amyloidoses are those that tend to involve a single organ system and include Alzheimer's disease (Aβ peptides), spongiform encephalopathies (prion), Parkinson's disease (α-synuclein), Huntington's disease (Huntingtin), type-2 diabetes (IAPP), medullary carcinoma of the thyroid (calcitonin fragment), and atrial amyloidosis (atrial natriuretic factor).

Inhibition of Aggregation-Mediated Proteotoxicity The disclosure provides methods of inhibiting aggregation-mediated proteotoxicity in a subject or inhibiting the onset of symptoms of an amyloid disease in a subject, including administering to the subject a composition comprising a compound described herein for practicing the disclosure. "Aggregation-mediated proteotoxicity" refers to the pathological outcomes associated with the intracellular and/or extracellular accumulation of insoluble fibrillar proteins (amyloid) in affected tissues and organs. By "inhibiting", with respect to inhibiting aggregation-mediated proteotoxicity or inhibiting the onset of symptoms of an amyloid disease, is intended (i) preventing or treating the pathological outcomes associated with the intracellular and/or extracellular accumulation of amyloid, for example, causing clinical symptoms of proteotoxicity or the amyloid disease not to develop in a subject that may be predisposed to the same but does not yet experience or display symptoms; (ii) restraining proteotoxicity or the amyloid disease, for example, arresting the development of the disease or its clinical symptoms; (iii) ameliorating proteotoxicity or the amyloid disease, for example, delaying onset of clinical symptoms in a susceptible subject or a reduction in severity of some or all clinical symptoms; or (iv) relieving proteotoxicity or the amyloid disease, for example, causing regression of some or all clinical symptoms.

As used herein, "subject" includes organisms in which aggregation-mediated proteotoxicity or amyloidosis can occur, or which are susceptible to amyloid diseases, for example, the amyloid diseases described herein. Thus, "subject" includes both human, laboratory and veterinary organisms, for example, humans, non-human primates, dogs, cats, mice, horses, cows, and the like. In one embodiment, the compounds described herein (e.g., having a general formula set forth by formula I or II) for practicing the disclosure prevent or inhibit amyloid protein assembly into insoluble fibrils which, in vivo, are deposited in various organs, or they facilitate clearance of pre-formed deposits or slow deposition in subjects already having amyloid deposits. In another embodiment, the compounds may also prevent amyloid protein, in its soluble, oligomeric form or in its fibrillar form, from binding or adhering to a cell surface and causing cell damage or toxicity. In yet another embodiment, the compounds may block amyloid-induced cellular toxicity. In still another embodiment, the compounds may block amyloid-induced neurotoxicity. In a further embodiment, the compounds may enhance clearance from a specific organ (e.g., the brain) or decrease concentration of amyloid protein in such a way that amyloid fibril formation is prevented in the target organ.

The disclosure overcomes deficiencies in the art and provides effective screening methods to identify agents that confer protective effects on neurons. The subject disclosure is based on a screening assay developed using the microscopic transparent roundworm *Caenorhabditis elegans* (*C. elegans*), which is a particularly useful model for studying neurodegeneration because it allows observation of changes in cells within the living worm over the time-period that it takes to develop from a single-cell zygote to a mature adult. These kinds of observations are extremely difficult in other animals and impossible in humans. As the genetics of *C. elegans* are well known, and as the entire genomic sequence has been mapped, the *C. elegans* based screening system of the disclosure provides a powerful screening/identifying tool.

The disclosure provides methods and kits useful for screening aggregation-mediated proteotoxicity using a transgenic non-human animal model. In one embodiment, the model comprises a nematode worm such as *Caenorhabditis elegans*. In this embodiment, the disclosure provides a transgenic *C. elegans* animals expressing human amyloidic proteins and a fluorescent indicator protein (e.g., GFP) operably linked to a heat shock protein that co-localizes with amyloid deposits. Induction of expression of an amyloidic protein and resulting deposits co-localizes with the HSP-GFP fusion construct. The deposition can then be localized using standard fluorescent microscopy. The methods can be performed in liquid culture and nematodes visualized in the presence and absence of a test compound. An compound that inhibits aggregation mediated protioteoxicity will have a reduced visual GFP (vGFP) in culture.

In one embodiment, the amyloidic protein is operably linked to a tissue specific promoter such as unc-54 or preferably myo-3. In one embodiment, a polynucleotide useful in the methods comprises a myo-3::Aβ1-42/let-858 3'UTR. A vector comprising this polynucleotide has the myo-3 body-wall specific myosin promoter and a long 3'-untranslated region, which makes the transgene's expression dependent on smg-1 function (e.g., nonsense-mediated mRNA decay). The smg-1 in transgenic nematode becomes inactive at the non-permissive temperature of 23 C, which allows the translation of the stabilized transgenes mRNA for human Aβ1-42 and association with HSP-GFP fusion construct.

Although the non-limiting specific examples set forth below utilize green fluorescent protein as a detectable marker in the transgenic nematode model of the disclosure other fluorescent proteins can be substituted by one of skill in the art. Some examples of detectable markers include yellow fluorescent proteins, blue fluorescent proteins and red fluorescent proteins. Other spectral variants, mutational variants and derivatives of such fluorescent proteins are also contemplated.

In one embodiment the detectable marker is under the control of a promoter. In specific embodiments the promoter is a tissue-specific promoter. In other specific embodiments, the tissue-specific promoter is a neuronal promoter. Some neuronal promoters contemplated as useful are promoters specific to dopamine neurons such as the dopamine transporter promoters and the tyrosine hydroxylase promoters. In one embodiment, the tissue specific promoter comprises a muscle tissue promoter (e.g., a myo-3 promoter).

Expression of the fluorescent marker by a tissue specific promoter allows for the expression of the marker in subsets of cells, such as in muscle cells. The skilled artisan will recognize that the disclosure is not limited to the use of the promoters described above and that any other Specific muscle, or other tissue specific promoter may be used in the practice of this disclosure. The goal is to obtain expression of a detectable marker in certain specific populations of cells.

The recombinant/transgenic C. elegans provided by the disclosure can also be used in methods of screening drugs and other agents to identify agents (e.g., small molecule agents, polynucleotides, polypeptides, peptidomimetics and the like) that can prevent or decrease aggregation mediated proteotoxicity.

Therefore, the disclosure further provides methods for screening for substances that affect aggregation mediated toxicity of peptides or proteins comprising: (a) providing a recombinant C. elegans that expresses a chaperone-related (e.g., HSP16.2) protein that associates with a protein/peptide that causes proteotoxicity wherein the chaperone-related protein is operably linked to a fluorescen marker and wherein the C. elegans comprises an inducible expression of a proteotoxic protein; (b) exposing the C. elegans to a candidate agent; and (c) detecting a change in the expression of the marker relative to the expression of the marker before the exposing, wherein a reduction in fluorescence (i.e., detection) of the marker corresponds to an agent that inhibits proteotoxicity or an agent that inhibits a neurodegenerative disease. Neurodegenerative diseases contemplated include, for example, Parkinson's disease, Alzheimer's disease, Huntington's disease, a transmissible spongiform encephalopathy, a familial amyloid polyneuropathy (FAP), a prion diseases, a Tauopathy, a Trinucleotide disease, amyotrophic lateral sclerosis (ALS) or multiple system atrophy.

A method for generating a recombinant nematode according to the disclosure can comprise introducing an expression construct, which contains a desired transgene or a desired nucleic acid sequence, into an hermaphrodite nematode. This can be effected, for example, by means of microinjection. After descendants have hatched from the eggs of the nematode, they are allowed to develop, after which at least one descendant, which contains the desired transgene or the desired nucleic acid under the control of regulatory sequences which permit an expression which is, where appropriate, tissue-specific or cell-specific, is identified. For the purpose of this identification, the expressed construct which is used for the transfection can additionally contain a marker gene which encodes a readily detectable marker protein, where appropriate as a fusion protein.

The nematode descendant which has been identified in this way can then, if desired or necessary, be subjected, where appropriate, to 4 further breeding procedure, for example crossing with other nematodes which, for example, are expressing other interesting transgenes, in order to produce lines which exhibit various desired properties in addition to the aberrant or nonexistent gene expression discussed above.

The delivery of agents to be tested (including RNAi molecules) can be performed by simple feeding of the nematode in a suitable bacterial strain. As a result of the worms growing on the bacteria, the agent or RNAi passes from the intestinal tract into the remaining cells, leading to the breakdown of the corresponding mRNA.

Although C. elegans is an exemplary species used in the methods of the disclosure, other recombinant/transgenic nematodes may be used. For example, nematodes of the genus Caenorhabditis include, for example C. elegans, C. vulgaris or C. briggsae.

The use of nematodes has numerous advantages, particularly for identifying and characterizing pharmaceuticals and active compounds. Nematodes according to the disclosure exhibit, in particular, symptoms which can be observed in a quite equivalent manner in human patients who are suffering from neurodegenerative diseases, including those in which plaque-like deposits appear in the nervous system, and, in particular, those patients who are suffering from Alzheimer's disease. Furthermore there these organisms can be produced in large numbers of identical transgenic descendants from one nematode allowing for the screening of a large numbers of pharmaceutical candidates or of whole libraries.

Screening can be carried out in microtiter plates either using agar or in soluble phase with 1 or more candidate agents per well of the plate. In one embodiment, a method of identifying a compound that inhibits aggregation-mediated proteotoxicity in a subject, includes: (1) providing a first C. elegans expressing a β-amyloid peptide; (2) determining the amount of fluorescence in the first C. elegans; (3) exposing a second C. elegans expressing the β-amyloid peptide to a test compound; (4) determining the fluorescence in the second C. elegans; and (5) comparing the levels of fluorescence in the first and second C. elegans, where the test compound is identified as a compound that inhibits aggregation-mediated proteotoxicity in a subject when the level of fluorescence in the second C. elegans is less than the level of fluorescence in the first C. elegans. In a non-limiting example, the β-amyloid peptide is expressed in body wall muscles.

Transgenic C. elegans strains have been engineered to express human proteins associated with neurodegenerative diseases. These model systems include transgenic worms expressing Aβ (Alzheimer's disease; see, e.g., Link, Proc. Natl. Acad. Sci. USA 92:9368-72, 1995; Link et al, Neurobiol. Aging 24:397-413, 2003), polyglutamine repeat proteins (Huntington's disease; see, e.g., Steffan and Thompson, Expert Opin. Ther. Targets 7:201-13, 2003), and α-synuclein (Parkinson's disease; see, e.g., Vartiainen et al., Exp. Gerontol. 41:871-76, 2006). In these invertebrate models, many aspects of the human diseases are reproduced. For example, transgenic C. elegans strain CL2006 constitutively expresses (under the direction of the unc-54 promoter) human Aβ1-42 within body wall muscles (i.e., those muscles below the neck), resulting in paralysis (Link, Proc. Natl. Acad. Sd. USA 92:9368-72, 1995). A similar phenotype is seen in *C. elegans* strain CL4176, where the expression of Aβ1-42 depends on a temperature up-shift from 16 to 23° C. (Link et al.; Neurobiol. Aging 24:397-413, 2003).

The disclosure is useful for screening lead compounds and derivatives thereof in the treatment and/or prevention of neurodegenerative diseases, including those in which plaque-like deposits appear in the nervous system, or substances which are suitable for modifying the effect of a pharmaceutical in the treatment and/or prevention of such diseases. For example, compounds can be derivatized to their corresponding salts, eterified, and the like and screened in the methods of the disclosure. For example, the method can be used to identify salts, enantiomers, and derivatives of compounds of formula I or II without undue experimentation. Hydroxyl groups which are present on the lead substance can be used, for example, for etherification or customary reactions of a different nature. The disclosure also encompasses any types of formation of additional compounds and solvates and of substitutions which can be performed on the backbone chain of a lead substance such as a compound of formula I or II, for example on an aromatic ring structure which is present in a chain. Substitutions of hydrogen atoms, halogen atoms, hydroxyl groups, amine groups, carboxylic acid groups or alkyl groups, or substitutions by such groups or atoms, can, for example, be performed.

Other assays for inhibiting aggregation of proteotoxic molecules can be performed simultaneously or in addition to the fluorescence techniques described herein. Furthermore, other transgenic organism or recombinant host cells can be used in additional to the nematode model described herein. Such methods typically analyze β-amyloid peptide aggregation.

As used herein, "β-amyloid peptide" includes any amyloidogenic peptide produced from APP. Native human APP is encoded by a single 400-kb gene comprised of 18 exons on chromosome 21. Alternative mRNA splicing gives rise to three APP isoforms. Two forms, APP751 and APP770 contain a Kunitz-protease inhibitor (KPI) region; the third, APP-695, lacks the KPI segment. Sequences of particular interest are those which are disease-linked. Examples of disease-linked mutations include: a mutation at codon 693 (of APP770), linked to Dutch congophilic angiopathy (Levy et al., Science 248:1124-26, 1990); a valine-isoleucine mutation at codon 717 (of APP770), linked to familial AD (Goate et al, Nature 349:704-06, 1991), enhanced Aβ1-42 production is reported for APP with this mutation (Cai et al., Science 259:514-16, 1993; Suzuki et al, Science 264:1335-40, 1994); a mutation wherein the valine at codon 717 is replaced by phenylalanine or glycine (Chartier-Harlin et al, Nature 353:844-46, 1991; Murrell et al, Science 254:97-99, 1991); a mutation wherein alanine is replaced by glycine at codon 692, causing both congophilic angiopathy and AD (Hendriks et al, Nature Gen. 1:218-21, 1992); a double mutation at codons 670 and 671, resulting in a substitution of the normal lysine-methionine dipeptide by asparagine-leucine (Mullan et al, Nature Gen. 1:345-47, 1992), APP with this double mutation is associated with increased Aβ secretion (Citron et al, Nature 360:672-74, 1992; Cai et al, Science 259:514-16, 1993). In some embodiments, β-amyloid peptide is a 39-43 amino acid peptide derived by proteolysis from APP, such as, for example, Aβ1-42.

"Determining the rate of paralysis" in *C. elegans* involves an assessment or measurement of muscle function in the worms as a function of time. For example, assessment or measurement of muscle function can be evaluated on a minute-by-minute basis, such as every minute, every five minutes, every ten minutes or every thirty minutes, or on an hourly basis, such as every hour, every two hours, every six hours, or every twelve hours. Assessment or measurement of muscle function can be by visual inspection or by automated means. In one embodiment, determining the rate of paralysis includes measurement of muscle function by visual inspection. In another embodiment, determining the rate of paralysis includes measurement of muscle function by an automated system.

Measurement of muscle function in *C. elegans* by visual inspection is a well known procedure to those of ordinary skill in the art, and includes probing (i.e., physically contacting) the worms, for example, with a pick, and looking for muscle contractions below the neck. In the absence of muscle contractions, the probing is generally repeated several more times (e.g., at the same and/or different locations on the worm) to ensure that there are no muscle contractions. The absence of muscle contractions indicates that the worm is paralyzed. Measurement of muscle function in *C. elegans* can also be automated. By "automated" is intended an assessment or measurement of muscle function by any means that reduces human operator involvement in the measurement and/or analysis of muscle function, and generally includes mechanical and/or electronic components. In one embodiment, automated measurement of muscle function in *C. elegans* includes measurement of Ca2+ flux within muscle cells. In another embodiment, automated measurement of muscle function in *C. elegans* includes measurement of the rate of ATP hydrolysis within muscle cells. In yet another embodiment, automated measurement of muscle function in. *C. elegans* includes measurement of one or more reporter proteins.

Measurement of $Ca^{2+}$ flux within muscle cells can be determined by methods well known to those of ordinary skill in the art, including, for example, $Ca^{2+}$ measurements with fluorescent indicators, such as fluorescent $Ca^{2+}$ indicators excited with UV light and fluorescent $Ca^{2+}$ indicators excited with visible light, and $Ca^{2+}$ measurements with bioluminescent indicators. Fluorescent probes that show a spectral response upon binding $Ca^{2+}$ enable investigations into changes in intracellular free $Ca^{2+}$ concentrations using fluorescence microscopy, flow cytometry and fluorescence spectroscopy. Exemplary UV light-excitable, ratiometric Ca+ indicators include fura-2, indo-1, fluo-3, fluo-4, Calcium Green, quin-2, fura-4F, fura-5F, fura-6F, and indo-5F (Invitrogen, Carlsbad, Calif.; see also, Haugland and Johnson, Intracellular Ion Indicators in Fluorescent and Luminescent Probes for Biological Activity, 2nd Ed., Mason, Ed., pp. 40-50, 1999). Exemplary visible light-excitable Ca2+ indicators include fluo-3, fluo-4, rhod-2, Calcium Green, Calcium Yellow, Calcium Orange, Calcium Crimson, and the Oregon Green 488 BAPTA indicators (Invitrogen, Carlsbad, Calif.). Aequorin, a photoprotein originally isolated from luminescent jellyfish and other marine organisms, is an exemplary bioluminescent Ca+ indicator (Invitrogen, Carlsbad, Calif.).

Measurement of the rate of ATP hydrolysis within muscle cells is also determined by methods well known to those of ordinary skill in the art. For example, the rate of ATP hydrolysis can be measured with an enzymatic-coupled β-NADH fluorometric technique in which the regeneration of ATP from ADP and phospho(e<<o/)pyruvate is catalyzed by pyruvate kinase (see, e.g., Kenney et al., Can. J. Physiol. Pharmacol. 72:1361-67, 1994). This reaction is coupled to the oxidation of NADH to NAD+ and to the reduction of pyruvate to lactate; these reactions are catalyzed by lactate dehydrogenase. For each mole of ADP produced, 1 mole of NADH, a fluorescent compound, is oxidized to NAD+, a nonfluorescent compound. Thus the rate of decrease in NADH fluorescence is proportional to the rate of ATP hydrolysis by the muscle cells.

Reporter proteins can also be used for automated measurement of muscle function in C. elegans. DNA microarray analysis of worms that express Aβ1-42 has revealed increased expression of several genes in response to Aβ1-42 expression. Under conditions of high Aβ1-42 proteotoxicity (i.e., paralysis), these genes are turned on, while they are turned off under conditions of low Aβ1-42 proteotoxicity (i.e., no paralysis). Reporter constructs containing the promoters of these genes operably-linked to a reporter of interest (e.g., luciferase or a fluorescent protein, such as green fluorescent protein (GFP)) can be used to monitor muscle function in an automated system. Such a system will include a means for analyzing reporter activity (as a surrogate for muscle function), such as a spectrophotometer or a fluorescence-activated cell sorter. In some embodiments, the C. elegans are deficient in the expression of one or more genes, such as, for example, one or more genes that regulate lifespan and/or youthfulness. In both mammals and worms, insulin/insulin growth factor (IGF)-1-like signaling (IIS) plays a prominent role in lifespan and youthfulness (Kenyon, Cell 120:449-60, 2005). In C. elegans, the sole insulin/IGF-1 receptor, DAF-2, initiates the transduction of a signal that causes the phosphorylation of the FOXO transcription factor. DAF-16, preventing its translocation to the nucleus (Lin et al., Nat. Genet. 28:139-45, 2001). This negative regulation of DAF-16 compromises expression of its target genes and shortens the worms' lifespans. Thus, knockdown of daf-2 expression creates long-lived, youthful worms (Kenyon et al., Nature 366:461-64, 1993). In worms, lifespan extension due to reduced daf-2 activity is also dependent upon Heat Shock Factor 1 (HSF-I), and increased expression oïhsf-1 extends worm lifespan in a daf-16 dependent manner (Hsu et al, Science 300:1142-45, 2003).

Without being bound by theory, it is believed that two opposing mechanisms, regulated by the IIS pathway, protect worms from aggregation-mediated proteotoxicity (e.g., Aβ1-42 mediated toxicity): the HSF-I transcriptome regulates the primary proteotoxicity protection pathway, a disaggregation process coupled to proteolysis of monomorized amyloid protein (e.g., whereas the DAF-16 transcriptome regulates an active aggregation process that converts the more toxic oligomeric amyloid aggregates (e.g., Aβ1-42 aggregates) into high molecular weight aggregates of lower toxicity (Cohen et al, Science 313:1604-10, 2006).

By "deficient" in expression, is intended any statistically significant lower level of gene expression than that seen in a control, such as 10% lower, 20% lower, 30% lower, 40% lower, 50% lower, 60% lower, 70% lower, 75% lower, 80% lower, 85% lower, 90% lower, 95% lower, or 100% lower. An assessment of gene expression can be achieved by any number of methods well known in the art, including, for example, measurement of RNA levels (e.g., using Northern blotting or reverse transcription PCR), measurement of protein levels (e.g., using Western blotting, or immunohistochemistry) and measurement of protein activity (e.g., measuring the disaggregation activity of HSF-I and/or the aggregation activity of DAF-16). Methods for determining disaggregation/aggregation activities are described elsewhere herein.

Knockdown of gene expression in C. elegans can be achieved by one of ordinary skill in the art using well known methods. For example, the level and/or activity of a polypeptide may be modulated by employing a polynucleotide that is not capable of directing, in a worm, the expression of a protein or an RNA. For example, polynucleotide constructs may be designed that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenie oligonucleobases. Such nucleotide constructs and methods of use are known in the art. See, e.g., U.S. Pat. Nos. 5,565,350; 5,731,181; 5,756,325; 5,760,012; 5,795,972; and 5,871,984. See also, WO 98/49350, WO 99/07865, WO 99/25821, and Beetham et al, Proc. Natl. Acad. Sci. USA 96:8774-78, 1999.

Many techniques for gene knockdown or silencing are well known to one of skill in the art, including, but not limited to, antisense technology (see, e.g., Sheehy et al., Proc. Natl. Acad. Sci. USA 85:8805-09, 1988; and U.S. Pat. Nos. 5,107, 065; 5,453,566; and 5,759,829); cosuppression (see, e.g., Jorgensen, Trends Biotech. 8:340-44, 1990; Flavell, Proc. Natl. Acad. Sci. USA 91:3490-96, 1994; Finnegan et al, Bio/Technology 12:883-88, 1994; and Neuhuber et al, Mol. Gen. Genet. 244:230-41, 1994); RNA interference (see, e.g., Napoli et al, Plant Cell 2:279-89, 1990; Sharp, Genes Dev. 13:139-41, 1999; Zamore et al, Cell 101:25-33, 2000; Montgomery et al, Proc. Natl. Acad. Sci. USA 95: 15502-507, 1998; and U.S. Pat. No. 5,034,323); virus-induced gene silencing (see, e.g., Burton et al, Plant Cell 12:691-705, 2000; and Baulcombe, Curr. Op. Plant Bio. 2: 109-13, 1999); target-RNA-specific ribozymes (see, e.g., Haseloff et al, Nature 334: 585-91, 1988); hairpin structures (see, e.g., Smith et al, Nature 407:319-20, 2000; Chuang and Meyerowitz, Proc. Natl. Acad. Sci. USA 97:4985-90, 2000; Stoutjesdijk et al, Plant Physiol. 129:1723-31, 2002; Waterhouse and Helliwell, Nat. Rev. Genet. 4:29-38, 2003; Panstruga et al, Mol. Biol. Rep. 30: 135-40, 2003; Wesley et al, Plant J. 27:581-90, 2001; Wang and Waterhouse, Curr. Opin. Plant Biol 5:146-50, 2001; WO 98/53083; WO 99/53050; and WO 02/00904); ribozymes (see, e.g., Steinecke et al, EMBO J. 11:1525-30, 1992; and Perriman et al, Antisense Res. Dev. 3:253-63, 1993); oligonucleotide-mediated targeted modification (see, e.g., WO 03/076574 and WO 99/25853); Zn-fmger targeted molecules (see, e.g., WO 01/52620; WO 03/048345; and WO 00/42219); and other methods or combinations of the above methods known to those of skill in the art.

In a non-limiting example, RNA interference (RNAi) is used to decrease the activity of a C. elegans gene, such as daf-2, hsf-1 and/or daf-16. Briefly, feeding worms bacteria expressing double-stranded RNA (dsRNA) for a gene of interest (e.g., daf-2, hsf-1 and/or daf-16 dsRNA) decreases the activity of the gene of interest. In a further embodiment, a method of identifying a compound that inhibits aggregation-mediated proteotoxicity in a subject, includes: (1) providing a first C. elegans expressing a β-amyloid peptide; (2) preparing an extract from the first C. elegans; (3) determining a disaggregation activity of the extract from the first C. elegans; (4) exposing a second C. elegans expressing the β-amyloid peptide to a test compound; (5) preparing an extract from the second C. elegans; (6) determining a disaggregation activity of the extract from the second C. elegans; and (7) comparing disaggregation activities of the extracts of the first and second C. elegans, where the test compound is identified as a compound that inhibits aggregation-mediated proteotoxicity in a subject when the disaggregation activity of the extract from the second C. elegans exceeds the disaggregation activity of the extract from the first C. elegans. In a non-limiting example, the β-amyloid peptide is expressed in body wall muscles.

By "determining a disaggregation activity" of an extract from a C. elegans is intended assessing the ability of an extract prepared from one or more worms to disaggregate amyloid fibrils, for example, β-amyloid fibrils such as Aβ1-42 fibrils. The worms can be wild-type *C. elegans*, worms treated with one or more test compounds and/or worms deficient in the expression of one or more genes. Methods for measuring disaggregation of amyloid fibrils are well known in the art. In one non-limiting example, post-debris supernatant (PDS) from homogenized worms is used in an in-vitro assay to measure disaggregation of amyloid fibrils (see, Cohen et al., Science 313:1604-10, 2006).

Briefly, time dependent disaggregation of pre-aggregated amyloid fibrils in-vitro, in the presence and absence of worm PDS is quantified. The pre-aggregated amyloid fibrils (e.g., Aβ1-42 fibrils) can be labeled, for example, with a fluorescent dye, such as Thioflavin-T. Thioflavin-T is used in the fluorometric determination of amyloid fibrils in-vitro. In the absence of amyloid fibrils, the dye fluoresces faintly at the excitation and emission maxima of 350 and 438 nm, respectively. In the presence of amyloid fibrils, there is a bright fluorescence with this dye at the excitation and emission maxima of 450 and 482 nm, respectively; fluorescence change is linear from 0 to 2.0 µg/ml of amyloid fibrils. One or more protease inhibitors can be included to exclude the possibility of monitoring proteasomal and/or proteolytic degradation, rather than disaggregation. Pre- and post-disaggregation samples can also be assayed by Western blot analysis, using an amyloid-specific antibody (e.g., an amyloid-specific monoclonal antibody) to visualize fibrillar and monomelic amyloid protein.

In yet a further embodiment, a method of identifying a compound that inhibits aggregation-mediated proteotoxicity in a subject, includes: (1) providing a *C. elegans* expressing a β-amyloid peptide; (2) preparing a plurality of equivalent extracts from the *C. elegans*; (3) determining a disaggregation activity of a first extract from the plurality of equivalent extracts; (4) exposing a second extract from the plurality of equivalent extracts to a test compound; (5) determining a disaggregation activity of the second extract; and (6) comparing disaggregation activities of the first and second extracts, where the test compound is identified as a compound that inhibits aggregation-mediated proteotoxicity in a subject when the disaggregation activity of the second extract exceeds the disaggregation activity of the first extract. In a non-limiting example, the β-amyloid peptide is expressed in body wall muscles.

In another embodiment, high throughput screening methods involve providing a combinatorial chemical library containing a large number of potential therapeutic compounds (i.e., compounds with the potential to inhibit aggregation-mediated proteotoxicity in a subject). Such combinatorial libraries are then screened in one or more assays as described herein to identify those library members (particularly chemical species or subclasses) that display a desired characteristic activity (such as inhibiting amyloid protein assembly into insoluble fibrils or facilitating clearance of pre-formed amyloid deposits). The compounds thus identified can serve as conventional "lead compounds" or can themselves be used in potential or actual pharmaceutical compositions. In some instances, pools of candidate compounds can be identify and further screened to determine which individual or subpools of compound(s) in the collective have the desired activity.

In another embodiment, a method of identifying a compound that inhibits aggregation-mediated proteotoxicity in a subject, includes: (1) providing a first mammal expressing a β-amyloid peptide; (2) preparing an extract from the first mammal; (3) determining a disaggregation activity of the extract from the first mammal; (4) exposing a second mammal expressing the β-amyloid peptide to a test compound; (5) preparing an extract from the second mammal; (6) determining a disaggregation activity of the extract from the second mammal; and (7) comparing disaggregation activities of the extracts of the first and second mammals, where the test compound is identified as a compound that inhibits aggregation-mediated proteotoxicity in a subject when the disaggregation activity of the extract from the second mammal exceeds the disaggregation activity of the extract from the first mammal. In a non-limiting example, the β-amyloid peptide is expressed within the brain.

Transgenic non-human mammals, generally rodents, such as a mouse, have been engineered to over or under express numerous proteins, including many proteins associated with neurodegenerative diseases and animal lifespan. These models include, for example, transgenic mice expressing Familial Alzheimer's Disease (FAD)-linked presenilin 1 (PS1) and presenilin 2 (PS2) variants (Borchelt et al., Neuron 17:1005-13, 1996) and APP/APP variants (Borchelt et al., Neuron 19:939-45, 1997), or both (Arendash et al, Brain Res. 891: 42-53, 2001), as well as IGF-I receptor knockout mice (Holzenberger et al., Nature 421: 182-87, 2003). A promoter from a gene expressed in a tissue of interest (e.g., the brain) in the host animal is employed for varying the phenotype of the transgenic animal.

A variety of promoter sequences can be used to control expression of coding sequences, such as APP coding sequences, in transgenic animals. These include, without limitation, the metallothionine promoter, from which expression can be regulated through modulation of zinc and glucocorticoid hormone levels (Palmiter et al., Nature 300:611-15, 1982); the rat neuron specific enolase gene promoter (Forss-Petter et al., Neuron 5:187-97, 1990); the human β-actin gene promoter (Ray et al., Genes Dev. 5:2265-73, 1991); the human platelet derived growth factor β chain gene promoter (Sasahara et al., Cell 64:217-27, 1991); the rat sodium channel gene promoter (Maue et al, Neuron 4:223-31, 1990); the human copper-zinc superoxide dismutase gene promoter (Ceballos-Picot et al, Brain Res. 552: 198-14, 1991); and promoters for members of the mammalian POU-domain regulatory gene family (Xi et al, Nature 340:35-42, 1989). The POU-domain is the region of similarity between the transcription factors Pit-1, Oct-1, Oct-2, and UNC-86, and represents a portion of the DNA-binding domain. These promoters provide for expression specifically within the neurons of transgenic animals.

Transgenic animals are prepared in a number of ways well known to the skilled artisan. A transgenic animal is one that has an extra or exogenous fragment of DNA in its genome. In order to achieve stable inheritance of the extra or exogenous DNA fragment, the integration event must occur in a cell type that can give rise to functional germ cells, either sperm or oocytes. Two animal cell types that can form germ cells and into which DNA can be introduced readily are fertilized egg cells and embryonic stem (ES) cells.

An exemplary method for making transgenic animals is by zygote injection, as described, for example, in U.S. Pat. No. 4,736,866. The method involves injecting DNA into a fertilized egg, or zygote, and then allowing the egg to develop in a pseudo-pregnant mother. The zygote can be obtained using male and female animals of the same strain or from male and female animals of different strains. The transgenic founder is bred to produce more animals with the same DNA insertion. In this method of making transgenic animals, the new DNA typically randomly integrates into the genome by a non-homologous recombination event. One to many thousands of copies of the DNA may integrate at one site in the genome.

Another method is to use ES cells, which can be returned from in vitro culture to a "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring.

In a similar fashion, knockout animals (both heterozygous knockouts and null mutants) can be produced. A exemplary method for making knockout animals uses a gene targeting vector that flanks an exon of the gene to be knocked out with a selectable cassette, such as a drug-resistance cassette (e.g., neomycin-resistance), and a pair of loxP sites. The drug-resistance cassette provides a useful means for screening and selection of positively targeted zygotes, and both it and the exon of the gene to be knocked out can be deleted by Cre-lox recombination, producing a knockout allele (see, e.g., Holzenberger et al, Endocrinology 141:2257-66, 2000; Holzenberger et al, Endocrinology 142:4469-78, 2001). Transgenic founder animals can be used to produce stable lines of transgenic animals that over or under express a protein of interest (e.g., native or a mutant forms APP), or have one or more genes knocked out. Behavioral studies can be used to evaluate one or more effects mediated by the transgene, such as one or more effects mediated by native or mutant forms of APP. Exemplary behavioral studies include, but are not limited to, memory tests, such as the submerged platform and fear conditioning tests, and motor skills tests, such as the rota-rod, string agility and beam balance tests.

The submerged platform (or water maze) test is used to measure acquisition and memory retention. For purposes of analysis, a circular pool floor is divided into four quadrants and an indiscernible platform is positioned in one of the quadrants below the water surface. Testing involves multiple trials per day over several days. In the course of daily testing, an animal is admitted successively into each of the quadrants and allowed to swim for a maximum time period (e.g., 60 seconds). Upon locating the platform (or after the maximum time period) the animal is permitted to remain on the platform for a time period (e.g., 30 seconds) prior to the next trial. Latency to find the platform for each of the trials and the average of the trials is recorded for each animal. On the day following the last day of acquisition testing, memory retention is determined in a single probe trial (e.g., 60 seconds). The submerged platform is removed from the water maze and the animal is released into the quadrant opposite that into which the submerged platform has been placed for the acquisition trials. Trials are recorded for subsequent analysis of swim path and swim speed. The percent of time spent in each quadrant is determined and statistically analyzed. See, for example, King et al., Behay. Brain Res. 103:145-62, 1999. The fear conditioning test is also used to measure acquisition and memory retention. Briefly, the acquisition of cue fear consists of two phases, fear acquisition and testing. Conditional fear acquisition is induced by presenting audible cues (e.g., a tone or white noise) that coterminates with mild foot shocks. Acquisition involves multiple repeats of the same cue. The time of freezing after the same cue (a consequence of fear) is recorded during the next several days; fear depends upon memory of the electric shocks. See, for example, King et al., Behay. Brain Res. 103:145-62, 1999 and Cain et al, J. Neurosci. 22:9113-21, 2002.

The rota-rod test, for evaluation of motor skills, is performed essentially as described by Lynch et al. (Brain Res. 83:249-59, 1975). Briefly, an animal is required to run on a treadmill (e.g., Rota-Rod, Ugo Basile, Comerio, Italy) for a set period of time (e.g., 3-5 minutes) to maintain its position on top of a rod revolving at a set or accelerating speed. The protocol ends when the animal falls, or when the time has expired (in which case the animal is put back on the rod each time it falls). Total time on the rod or total number of falls are recorded and statistically analyzed. The string agility test is also a well known method of evaluating motor skills.

In order to measure forepaw grip capacity and agility, string (e.g., cotton string) is tautly suspended above a padded surface. Initially, an animal is permitted to grasp the string only by the forepaws, and then is released. In the course of a trial period (e.g., 60 seconds), a rating system is used to assess each animal, 0: animal unable to remain on string following release; 1: animal hangs by two forepaws for approximately 60 seconds; 2: animal attempts to climb string; 3: animal places two forepaws and one or both hindpaws around string; 4: animal places four paws and tail around string with lateral movement; and 5: animal escapes. See, for example, King et al., Behay. Brain Res. 103:145-62, 1999.

An additional well known test for evaluating motor skills is the beam balance test. A narrow dowel beam (e.g., about 1 cm wide) is fixed between two support columns above a padded surface. At either end of the beam is attached a platform. Each animal is administered several trials (e.g., three) during a single day of testing. The animal is placed in a perpendicular orientation at the center of the beam and released for a trial interval period (e.g., 60 seconds). The time required for the animal to fall from the beam is noted for each of the several trials. Alternatively, if the animal remains on the beam for the duration of the trial period, or escapes to either platform, the maximum interval period is recorded. The score for each trial, the average of the several trials and the number of escapes are recorded for each animal. See, for example, King et al, Behay. Brain Res. 103: 145-62, 1999.

Transgenic animals are also observed clinically to determine, inter alia, the age of onset of one or more effects mediated by the transgene, the duration of the one or more effects, the penetrance of the phenotype, and systemic or regional organ dysfunction (e.g., brain dysfunction). As discussed herein, an assessment of gene expression can be achieved by any number of methods well known in the art, including, for example, measurement of RNA levels (e.g., using Northern blotting or reverse transcription PCR), measurement of protein levels (e.g., using Western blotting, or immunohistochemistry) and measurement of protein activity. Various changes in phenotype are of interest. For example, in transgenic animals with modified APP expression, these changes may include progressive neurologic disease in the cortico-limbic areas of the brain expressed within a short period of time from birth, increased levels of expression of an APP gene above endogenous expression levels (generally accompanied by the development of a neurologic illness and premature death), gliosis and intracellular APP/Aβ accretions present in the hippocampus and cerebral cortex, diminished 2-deoxyglucose uptake/utilization and hypertrophic gliosis in the cortico-limbic regions of the brain, progressive neurologic disease characterized by diminished exploratory/locomotor behavior, and impaired performance on memory and learning tests.

Regions known to be affected by the amyloid disease of interest (e.g., the brain) are particularly reviewed for changes. When the amyloid disease of interest is AD, the regions reviewed include the cortico-limbic region, including APP/Aβ excretions, gliosis, changes in glucose uptake and utilization, and Aβ plaque formation. However, in strains of animals which are not long-lived, either naturally or when expressing high levels of APP, not all behavioral and/or pathological changes associated with a particular amyloid disease may be observed. For example, transgenic FVB/N mice expressing high levels of APP tend not to develop detectable Aβ plaques, whereas longer lived C57B6/SJL F1 mice expressing identical transgenes do develop amyloid plaques which are readily detected with Thioflavin-T and Congo red. Immunologic studies of various brain regions also are used to detect transgene product.

Using the methods of the disclosure a number of compounds were identified that are useful for inhibiting aggregation mediated proteotoxicity. An exemplary compound identified by the method of the disclosure is a compound having general formula I:

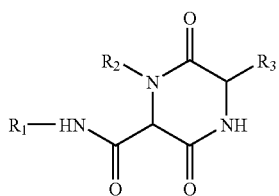

(I)

wherein $R_1$ is aryl, heteroaryl, arylalkyl, or heteroarylalkyl, each optionally substituted; $R_2$ is alkyl, substituted alkyl, aryl, substituted aryl, heteroaryl or substituted heteroaryl; $R_3$ has a formula selected from the group consisting of —$R_4$—X—$R_5$ and —C(R)$_2$—C(R)$_2$—C(R)$_2$—$R_6$; $R_4$ is a bond, alkyl, substituted alkyl, aryl or substituted aryl; $R_5$ is H, alkyl, substituted alkyl, aryl, or substituted aryl; X is selected from the group consisting of O, S, N(R), C(O), C(O)NR, and S(O)$_n$, wherein n is 0, 1 or 2; $R_6$ is selected from the group consisting of aryl, optionally substituted aryl, heteroaryl, and substituted heteroaryl; and each R is independently selected from the group consisting of H, aryl, substituted aryl, alkyl, or substituted alkyl; or a salt of any of the foregoing compounds. In one embodiment, $R_1$ is arylalkyl or substituted arylalkyl. In another embodiment, $R_1$ is phenylmethyl or substituted phenylmethyl. In a further embodiment, $R_2$ is alkyl or substituted alkyl. In yet another embodiment, $R_2$ is selected from the group consisting of arylalkyl, substituted arylalkyl, heteroarylalkyl and substituted heteroarylalkyl. In yet another embodiment, $R_2$ is phenylmethyl or substituted phenylmethyl. In yet a further embodiment, $R_2$ is pyridylmethyl or substituted pyridylmethyl. In one embodiment, $R_2$ is alkyl substituted with heterocycle, wherein said alkyl or heterocycle are each optionally substituted. In another embodiment, X is O. In yet another embodiment, $R_5$ is an alcohol protecting group. In yet a further embodiment, $R_5$ is selected from the group consisting of acetyl (Ac), benzoyl (Bz), benzyl (Bn), β-methoxyethoxymethyl ether (MEM), dimethoxytrityl[bis-(4-methoxyphenyl)phenylmethyl, DMT], methoxymethyl ether (MOM), methoxytrityl[(4-methoxyphenyl)diphenylmethyl, MMT), p-methoxybenzyl ether (PMB), methylthiomethyl ether; pivaloyl (Piv), tetrahydropyranyl (THP), trityl (triphenylmethyl, Tr), silyl ether (e.g., trimethylsilyl (TMS), tert-butyldimethylsilyl (TBDMS), tert-butyldimethylsilyloxymethyl (TOM), and triisopropylsilyl (TIPS) ethers), a methyl ethers and ethoxyethyl ethers (EE).

In yet another embodiment, the disclosure provides a compound of Formula II:

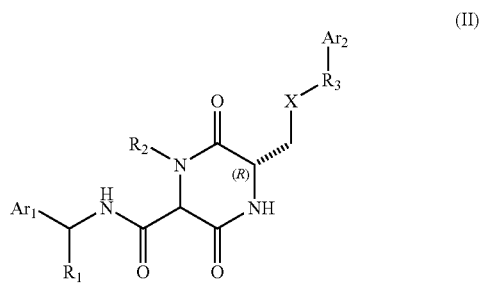

(II)

Wherein $Ar_1$ is a phenyl or substituted phenyl group, wherein $R_1$ is H, —CH$_3$, or SO$_2$R, wherein R is H, aryl, substituted aryl, alkyl, or substituted alkyl; wherein $R_2$ is any alkyl, aryl, heteroaryl; wherein X is O, S, or NH, wherein $R_3$ is (CH$_2$)$_n$, and n is 0-3 when X=O or S or $R_3$=C=O where X is NH; wherein $Ar_2$ is any aryl or heteroaryl and any salts of any of the foregoing. For example, compounds of formula I or II include, but are not limited to:

A7

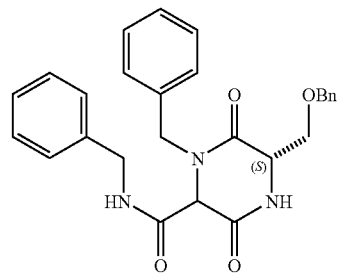

Mol. Wt.: 457.52
CLogP: 3.94845

E7

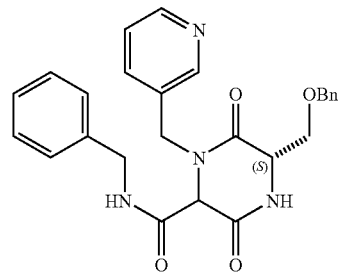

Mol. Wt.: 458.51
CLogP: 2.45145

B7

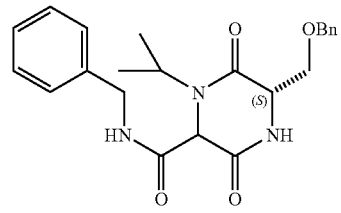

Mol. Wt.: 409.48
CLogP: 3.2295

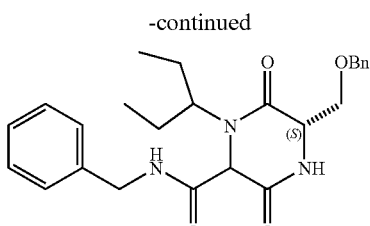

Mol. Wt.: 437.53
CLogP: 4.2875

C7

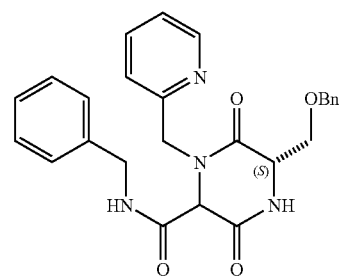

Mol. Wt.: 458.51
CLogP: 2.45145

G7

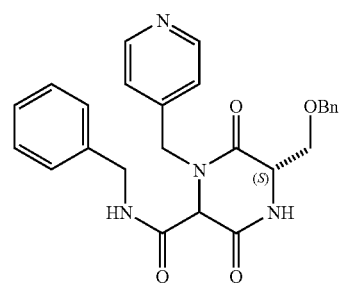

Mol. Wt.: 458.51
CLogP: 2.45145

D7

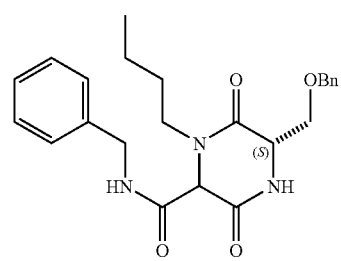

Mol. Wt.: 423.5
CLogP: 3.9785

H7

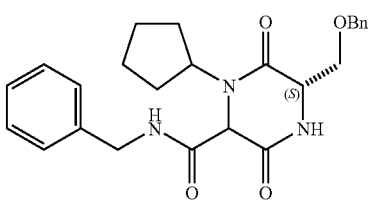

Mol. Wt.: 435.52
CLogP: 3.74545

Alkyl groups include straight-chain, branched and cyclic alkyl groups. As used herein, the term "alkyl" expressly encompasses alkenyl. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups; Cyclic alkyl groups can include bicyclic and tricyclic alkyl groups. Alkyl groups optionally include substituted alkyl groups. Substituted alkyl groups include, among others, those which are substituted with aryl groups, which in turn can be optionally substituted. Specific examples of alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which can be optionally substituted. The term "cyclopentyl ring" refers to a ring of five carbons with any degree of unsaturation. The term "cyclohexyl ring" refers to a ring of six carbons with any degree of unsaturation.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include, among others, those which are substituted with alkyl or aryl groups, which groups in turn can be optionally substituted. Specific examples of alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which can be optionally substituted.

The term "aryl" encompasses carbocyclic aromatic groups containing one or more rings. Thus, as used herein, the term "aryl" expressly encompasses monocyclic carbocyclic aromatic rings (e.g. phenyl) and bicyclic carbocyclic aromatic rings (e.g. naphthyl). Carbocyclic aromatic rings may be optionally substituted, e.g., by one or more $C_{1-6}$ alkyl $C_{2-6}$ alkenyl, halogen, aryloxy, thioaryl, cyano, hydroxy, nitro and the like. Substituted aryl groups include, among others, those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Heteroaryl groups include groups having one or more 5- or 6-member aromatic or heteroaromatic rings. Heteroaryl groups may be optionally substituted, e.g., by one or more $C_{1-6}$ alkyl $C_{2-6}$ alkenyl, halogen, aryloxy, thioaryl cyano, hydroxy, nitro and the like. Reference to "heteroaryl" include references to mono- and bicyclic heterocyclic aromatic rings containing 1-3 hetero atoms selected from nitrogen, oxygen and sulphur. Examples of monocyclic heterocyclic aromatic rings include e.g. pyridinyl, pyrimidinyl, thiophenyl, furanyl, pyrrolyl, oxazolyl, isoxazolyl, oxadiazolyl, thiazolyl, thiadiazolyl or imidazolyl, and examples of bicyclic heterocyclic aromatic rings include e.g. benzimidazolyl, or indolyl. Heteroaromatic rings can include one or more N, O, or S atoms in the ring. Heteroaromatic rings can include those with one, two or three N, those with one or two O, and those with one or two S.

Arylalkyl and heteroarylalky groups are expressly encompassed by the term "substituted alkyl." Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Heteroarylalkyl groups are alkyl groups substituted with one or more heteroaryl groups, wherein the alkyl groups optionally carry additional substituents and the aryl groups are optionally substituted.

Alkylaryl groups and alkylheteroaryl are expressly encompassed by the term "substituted aryl." Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl. Alkylheteroaryl groups are heteroaryl groups substituted with one or more alkyl groups wherein the alkyl groups optionally carry additional substituents and the aryl groups are optionally substituted.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups, heteroaryl groups, heterocyclic groups, each optionally substituted, or a combination thereof. Optional substitution of alkenyl groups further includes substitution with one or more alkyl groups, aryl groups, or both, wherein the alkyl groups or aryl groups are optionally substituted. Optional substitution of aryl groups further includes substitution of the aryl ring with one or more alkyl groups, alkenyl groups, or both, wherein the alkyl groups or alkenyl groups are optionally substituted.

Optional substituents for alkyl, alkenyl and aryl groups include, among others:

—COOR$_a$ where R$_a$ is a hydrogen or an alkyl group or an aryl group; and more specifically, where R$_a$ is methyl, ethyl, propyl, butyl, or phenyl groups all of which are optionally substituted;

—COR$_a$ where R$_a$ is a hydrogen, or an alkyl group or an aryl groups; and more specifically where R$_a$ is methyl, ethyl, propyl, butyl, or phenyl groups all of which groups are optionally substituted;

—CON(R$_a$)$_2$ where each R$_a$, independently of each other R$_a$, is a hydrogen or an alkyl group or an aryl group and more specifically where R$_a$ is methyl, ethyl, propyl, butyl, or phenyl groups all of which groups are optionally substituted; R$_a$ and R$_a$ can form a ring which may contain one or more double bonds;

—OCON(R$_a$)$_2$ where each R$_a$, independently of each other R, is a hydrogen or an alkyl group or an aryl group and more specifically where R is methyl, ethyl, propyl, butyl, or phenyl groups all of which groups are optionally substituted; R$_a$ and R$_a$ can form a ring which may contain one or more double bonds;

—N(R)$_2$ where each R, independently of each other R$_a$, is a hydrogen, or an alkyl group, acyl group or an aryl group and more specifically where R$_a$ is methyl, ethyl, propyl, butyl, or phenyl or acetyl groups all of which are optionally substituted; or R$_a$ and R$_a$ can form a ring which may contain one or more double bonds. —SR$_a$, —SO$_2$R$_a$, or —SOR$_a$ where R$_a$ is an alkyl group or an aryl groups and more specifically where R$_a$ is methyl, ethyl, propyl, butyl, phenyl groups all of which are optionally substituted; for —SR$_a$, R$_a$ can be hydrogen;

—OCOOR$_a$ where R$_a$ is an alkyl group or an aryl groups;

—SO$_2$N(R$_a$)$_2$ where R$_a$ is a hydrogen, an alkyl group, or an aryl group and adjacent R$_a$ groups can form a ring;

—OR$_a$ where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups as well as benzyl, pyridyl, pyridylmethyl and heterocycle, each optionally substituted. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

The term "heteroaryl" means a monocyclic- or polycyclic aromatic ring comprising carbon atoms, hydrogen atoms, and one or more heteroatoms, typically, 1 to 3 heteroatoms, independently selected from nitrogen, oxygen, and sulfur. As is well known to those skilled in the art, heteroaryl rings have less aromatic character than their all-carbon counter parts. Thus, for the purposes of the disclosure, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Typically, a heteroaryl group is a monocyclic ring, wherein the ring comprises 2 to 5 carbon atoms and 1 to 3 heteroatoms, referred to herein as "(C$_2$-C$_5$)heteroaryl".

As used herein "alcohol protecting groups" refer to a group introduced into a molecule by chemical modification of a functional group in order to obtain chemoselectivity in a subsequent chemical reaction and to prevent modification under certain conditions. Exemplary alcohol protecting group useful in the compounds and methods of the disclosure include, but are not limited to, acetyl (Ac), benzoyl (Bz), benzyl (Bn), β-methoxyethoxymethyl ether (MEM), dimethoxytrityl[bis-(4-methoxyphenyl)phenylmethyl, DMT], methoxymethyl ether (MOM), methoxytrityl[(4-methoxyphenyl)diphenylmethyl, MMT), p-methoxybenzyl ether (PMB), methylthiomethyl ether, pivaloyl (Piv), tetrahydropyranyl (THP), trityl (triphenylmethyl, Tr), silyl ether (e.g., trimethylsilyl (TMS), tert-butyldimethylsilyl (TBDMS), tert-butyldimethylsilyloxymethyl (TOM), and triisopropylsilyl (TIPS) ethers), a methyl ethers and ethoxyethyl ethers (EE).

Pharmaceutically acceptable salts comprise pharmaceutically-acceptable anions and/or cations. Pharmaceutically-acceptable cations include among others, alkali metal cations (e.g., Li+, Na+, K+), alkaline earth metal cations (e.g., Ca$^{2+}$, Mg$^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl—, Br—), sulfate, acetates (e.g., acetate, trifluoroacetate), ascorbates, aspartates, benzoates, citrates, and lactate.

Furthermore, compounds of the disclosure can have prodrug forms. Prodrugs of the compounds of the disclosure are useful in the methods of the disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The compounds of formula I or II are useful in preventing or inhibiting aggregated proteiotoxicity. The disclosure also provides compounds comprising the following structures. Such compounds are useful inhibitors of aggregated proteotoxicity. The methods and compositions of the disclosure include enantiomers, pharmaceutically acceptable salts and derivatives of a compound having the Formula I or II. Exemplary compounds of the invention include those set forth below:

A7

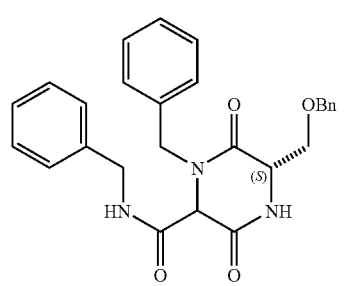

Mol. Wt.: 457.52
CLogP: 3.94845

E7

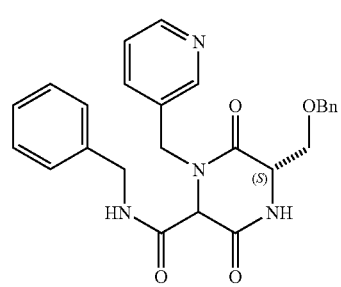

Mol. Wt.: 458.51
CLogP: 2.45145

B7

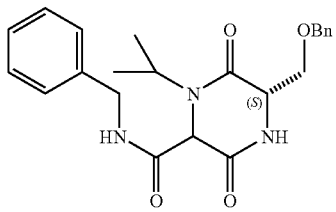

Mol. Wt.: 409.48
CLogP: 3.2295

F7

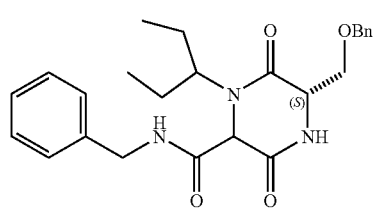

Mol. Wt.: 437.53
CLogP: 4.2875

C7

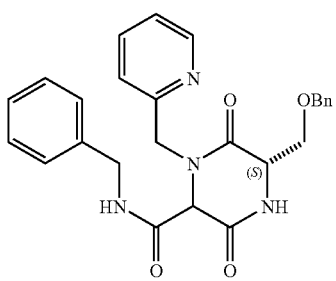

Mol. Wt.: 458.51
CLogP: 2.45145

G7

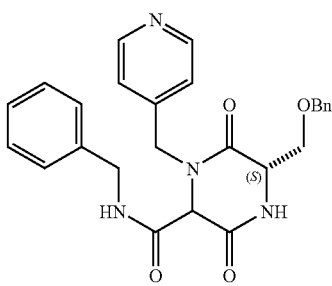

Mol. Wt.: 458.51
CLogP: 2.45145

D7

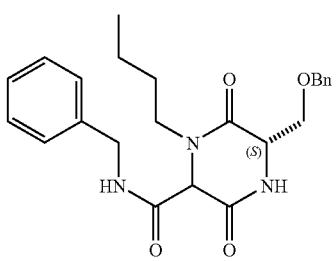

Mol. Wt.: 423.5
CLogP: 3.9785

-continued
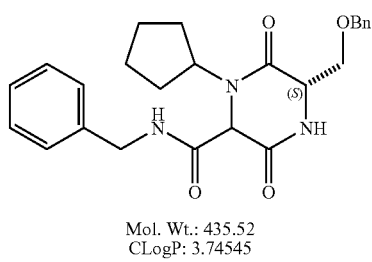
Mol. Wt.: 435.52
CLogP: 3.74545
Scheme I below depicts a Ugi reaction used to synthesize compounds of the disclosure.
Diketopiperazine-Ugi 4MCR, aka the Hulme Reaction
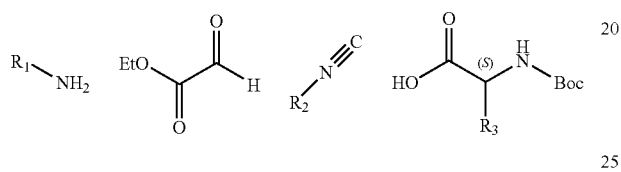
A classic 4-component Ugi reaction with post rxn scavenging, then cyclization. 0.1 mmol/well.
SCHEME I
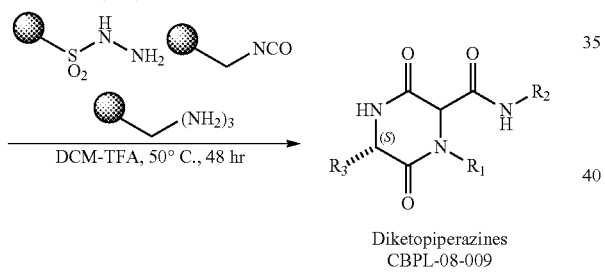
Diketopiperazines
CBPL-08-009
Amine
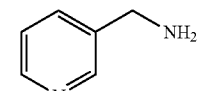 rA
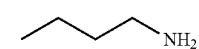 rE
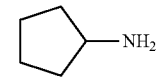 rB
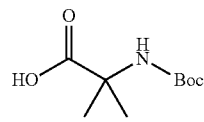 rF
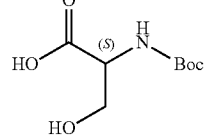 rC
-continued
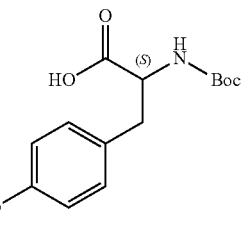 rG
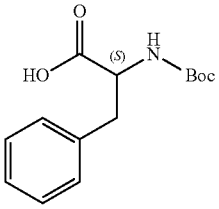 rD
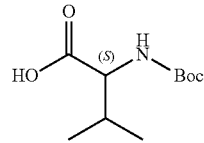 rH
Amino Acids
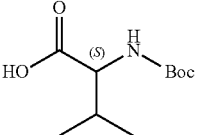 c1, c2
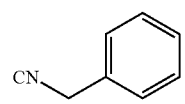 c7, c8
 c3, c4
 c9, c10
 c5, c6
 c11, c12
Isonitriles
 c1, c7

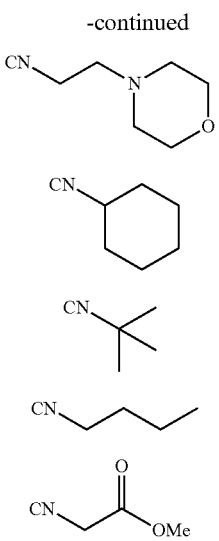

In addition to the compounds specifically noted above, the assays described according to the disclosure are also useful for identifying further compounds having activity for use in treatment of various disorders, such as neurodegenerative diseases, such activity arising from modulation of one or more aspects of aggregation-mediated proteotoxicity. As noted in relation to the above compounds, the activity of the compounds of the disclosure can include prevention or inhibition of amyloid protein assembly into insoluble fibrils, clearance of pre-formed deposits or slowing deposition in subjects already having amyloid deposits. The activity of the compounds may also include prevention of amyloid protein, in its soluble, oligomeric form or in its fibrillar form, from binding or adhering to a cell surface and causing cell damage or toxicity, or enhancing amyloid clearance from a specific organ (e.g., the brain).

The compounds provided above according to Formula I or II are not intended to limit the scope of active compounds provided according to the disclosure. On the contrary, the disclosure encompasses the additional compounds recited herein, multiple variants of the recited compounds, as well as further compounds identifiable according to the methods and assays described herein. In particular, the disclosure also encompasses pharmaceutically acceptable esters, amides, salts, or solvates of the various compounds described herein.

Biologically active variants of the compounds described herein for practicing the disclosure are particularly also encompassed by the disclosure. Such variants should retain the biological activity of the compounds described herein (i.e., the ability to inhibit aggregation-mediated proteotoxicity). According to one embodiment of the disclosure, suitable biologically active variants comprise analogues and derivatives of the compounds described herein for practicing the disclosure. As used herein, an "analogue" refers to a compound in which one or more individual atoms or functional groups have been replaced, either with a different atom or a different functional, generally giving rise to a compound with similar properties. Indeed, a single compound, such as those described herein, may give rise to an entire family of analogues having similar activity and, therefore, usefulness according to the disclosure. Likewise, a single compound, such as those described herein, may represent a single family member of a greater class of compounds useful according to the disclosure. Accordingly, the disclosure fully encompasses not only the compounds described herein, but analogues of such compounds, particularly those identifiable by methods commonly known in the art and recognizable to the skilled artisan.

A "derivative", as used herein, comprises a compound that is formed from a similar, beginning compound by attaching another molecule or atom to the beginning compound. Further, derivatives, according to the disclosure, encompass one or more compounds formed from a precursor compound through addition of one or more atoms or molecules or through combining two or more precursor compounds.

The disclosure also includes stereoisomers of the compounds described herein for practicing the disclosure, where applicable, either individually or admixed in any proportions. Stereoisomers may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the disclosure. Isomers may include geometric isomers. Examples of geometric isomers include, but are not limited to, cis isomers or trans isomers across a double bond. Other isomers are contemplated among the compounds of the disclosure. The isomers may be used either in pure form or in admixture with other isomers of the compounds described herein. The disclosure further includes prodrugs and active metabolites of the compounds described herein for practicing the disclosure. A prodrug includes any compound which, when administered to a subject, is converted in whole or in part to a compound as described herein. An active metabolite is a physiologically active compound which results from the metabolism of a compound described herein for practicing the disclosure, or a prodrug thereof, when such compound or prodrug is administered to a subject.

In some embodiments, a therapeutically effective amount of a compound of the disclosure is administered to a subject to inhibit aggregation-mediated proteotoxicity or the onset of symptoms of an amyloid disease. A "therapeutically effective amount" of a composition comprising formula I or II is an amount which, when administered to a subject, is sufficient to achieve a desired effect in a subject being treated with that composition. For example, this may be the amount of a composition useful in preventing, ameliorating and/or treating disease associated with amyloid fibril formation, aggregation or deposition in a subject. Ideally, a therapeutically effective amount of a composition comprising a formula I or II is an amount sufficient to prevent, ameliorate and/or treat disease associated with amyloid fibril formation, aggregation or deposition in a subject without causing a substantial cytotoxic effect in the subject.

The effective amount of a composition comprising a compound of formula I useful for preventing, ameliorating and/or treating disease associated with amyloid fibril formation, aggregation or deposition in a subject will depend on the subject being treated, the specific type and severity of the affliction and the manner of administration of the composition. Responses to a therapeutically effective amount of a composition comprising a compound of formula I or II can include, for instance, inhibition of amyloid protein assembly into insoluble fibrils, clearance of pre-formed deposits or a decrease in the rate of deposition of amyloid deposits. As described herein, the disclosure contemplates pharmaceutical compositions comprising a compound of formula I or II. Additional agents can include, for example, a flavone, a biguanide, a furanoflavonoid, 5-Aminoimidazole-4-carboxamide 1-β-D-ribofuranoside, trimethadione, and morin. Delivery systems and treatment regimens useful for such compounds are known and can be used to administer these compounds as therapeutics. In addition, representative embodiments are described herein.

The compounds described herein for practicing the disclosure can be administered in the form of an ester, amide, salt, solvate, prodrug, metabolite, derivative, or the like, provided it maintains pharmacological activity according to the disclosure. Esters, amides, salts, solvates, prodrugs, and other derivatives of the compounds of the disclosure may be prepared according to methods generally known in the art, such as, for example, those methods described by J. March, Advanced Organic Chemistry: Reactions, Mechanisms and Structure, 4th Ed. (New York: Wiley-Interscience, 1992).

Examples of pharmaceutically acceptable salts of the compounds described herein for practicing the disclosure include acid addition salts. Salts of non-pharmaceutically acceptable acids, however, may be useful, for example, in the preparation and purification of the compounds. Suitable acid addition salts according to the disclosure include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound described herein for practicing the disclosure may be prepared in a similar manner using a pharmaceutically acceptable base, such as sodium hydroxide, potassium hydroxide, ammonium hydroxide, calcium hydroxide, triethylamine, or the like. Esters of the compounds described herein for practicing the disclosure may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the disclosure can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the disclosure in combination with water, isopropanol, ethanol, methanol, DMSO, ethyl acetate, acetic acid, or ethanolamine.

Methods of administering a composition comprising a compound described herein for practicing the disclosure include, but are not limited to, intrathecal, intradermal, intramuscular, intraperitoneal, intravenous, subcutaneous, intranasal, epidural, intradural, intracranial, intraventricular, and oral routes. A composition comprising a compound described herein for practicing the disclosure may be administered by any convenient route, including, for example, infusion or bolus injection, topical, absorption through epithelial or mucocutaneous linings (for example, oral mucosa, rectal and intestinal mucosa, and the like) ophthalmic, nasal, and transdermal, and may be administered together with other biologically active agents. Administration can be systemic or local. In some instances, injection may be facilitated by a catheter, for example, attached to a reservoir. Pulmonary administration can also be employed (for example, by an inhaler or nebulizer), for instance using a formulation containing an aerosolizing agent.

In a specific embodiment, it may be desirable to administer a pharmaceutical composition locally to the area in need of treatment. This may be achieved by, for example, and not by way of limitation, local or regional infusion or perfusion during or following surgery, topical application (for example, wound dressing), injection, catheter, suppository, or implant (for example, implants formed from porous, non-porous, or gelatinous materials, including membranes, such as sialastic membranes or fibers), and the like. In one embodiment, a pump may be used (see, e.g., Langer, Science 249: 1527-33, 1990; Sefton, Crit. Rev. Biomed. Eng. 14:201-40, 1987; Buchwald et al., Surgery 88:507-16, 1980; Saudek et al., N. Engl. J. Med. 321:574-79, 1989). In one specific example, administration is achieved by intravenous, intradural, intracranial, intrathecal, or epidural infusion of a pharmaceutical composition using a transplanted minipump. Such minipump may be transplanted in any location that permits effective delivery of the therapeutic agent to the target site. In another embodiment, administration can be by direct injection at the site (or former site) of a tissue that is to be treated. In another embodiment, a pharmaceutical composition is delivered in a vesicle, in particular liposomes (see, e.g., Langer, Science 249: 1527-33, 1990; Treat et al, in Liposomes in the Therapy of Infectious Disease and Cancer, Lopez-Berestein and Fidler (eds.), Liss, N.Y., pp. 353-365, 1989).

In yet another embodiment, a pharmaceutical composition can be delivered in a controlled release system. In another embodiment, polymeric materials can be used (see, e.g., Ranger et al., Macromol. Sci. Rev. Macromol. Chem. 23:61-67, 1983; Levy et al, Science 228: 190-02, 1985; During et al, Ann. Neurol. 25:351-56, 1989; Howard et al., J. Neurosurg. 71:105-12, 1989). Other controlled release systems, such as those discussed in the review by Langer (Science 249: 1527-33, 1990), can also be used.

The vehicle in which a compound described herein for practicing the disclosure is delivered can include pharmaceutically acceptable compositions known to those of skill in the art. For instance, in some embodiments, compounds described herein for practicing the disclosure are contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The pharmaceutical composition, if desired, can also contain minor amounts of wetting or emulsifying agents, or pH buffering agents. The pharmaceutical composition can take the form of solutions, suspensions, emulsion, tablets, pills, capsules, powders, sustained-release formulations, and the like. The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: The Science and Practice of Pharmacy (19 Edition, 1995) in chapter 95.

Compositions comprising a compound described herein for practicing the disclosure can be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

The ingredients in various embodiments are supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to administration.

The amount of a compound described herein for practicing the disclosure that will be effective depends on the nature of the amyloid disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is from about 1 mg/day to about 1000 mg/day, including about 10 mg/day, 20 mg/day, 30 mg/day, 40 mg/day, 50 mg/day, 60 mg/day, 70 mg/day, 80 mg/day, 90 mg/day 100 mg/day, 125 mg/day, 150 mg/day, 175 mg/day, 200 mg/day, 225 mg/day, 250 mg/day, 275 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, and other such values between about 1 mg/day to about 1000 mg/day, for a patient having approximately 70 kg body weight, in single or divided doses. In some particular embodiments, a target concentration of a flavone, a biguanide, a furanoflavonoid, 5-Aminoimidazole-4-carboxamide 1-β-D-ribofuranoside, trimethadione, or morin in a target cell or tissue is between 0.1 and 10 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the amyloid condition of the host undergoing therapy.

The compositions comprising a compound described herein for practicing the disclosure can be administered at about the same dose throughout a treatment period, in an escalating dose regimen, or in a loading-dose regime (for example, in which the loading dose is about two to five times the maintenance dose). In some embodiments, the dose is varied during the course of a treatment based on the condition of the subject being treated, the severity of the amyloid disease or condition, the apparent response to the therapy, and/or other factors as judged by one of ordinary skill in the art. In some embodiments long-term treatment with a disclosed compound described herein for practicing the disclosure is contemplated.

In another embodiment of the disclosure, the pharmaceutical composition comprising the therapeutically effective dose of a compound described herein, such as a compound of formula I, for practicing the disclosure is administered intermittently. By "intermittent administration" is intended administration of a therapeutically effective dose of a compound described herein for practicing the disclosure, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the compound described herein for practicing the disclosure. The time period of discontinuance may be longer or shorter than the period of continuous sustained-release or daily administration. During the time period of discontinuance, the level of the compound in the relevant tissue is substantially below the maximum level obtained during the treatment. The preferred length of the discontinuance period depends on the concentration of the effective dose and the form of compound used. The discontinuance period can be at least two days, at least four days or at least one week. In other embodiments, the period of discontinuance is at least one month, two months, three months, four months or greater. When a sustained-release formulation is used, the discontinuance period can be extended to account for the greater residence time of the compound. Alternatively, the frequency of administration of the effective dose of the sustained-release formulation can be decreased accordingly. An intermittent schedule of administration of a compound described herein for practicing the disclosure can continue until the desired therapeutic effect, and ultimately treatment of the disease or disorder, is achieved.

Treatment of an amyloid disease as described herein include a method of inhibiting the onset of symptoms of an amyloid disease in a subject, comprising administering to the subject a therapeutically effective amount of a composition comprising a compound described herein (e.g., a compound of formula I) for practicing the disclosure. In one embodiment, the amyloid disease is a neurodegenerative disease that affect brain function, including conditions affecting movement, conditions affecting memory and conditions related to dementia. The area of the brain affected in a neurodegenerative disease may be the stroma including the vasculature, or the parenchyma including functional or anatomical regions, or neurons themselves.

In one embodiment of the disclosure, the subject to be treated is a human, for example, a human at risk for Alzheimer's disease. Alzheimer's disease is a neurodegenerative disease characterized by progressive cognitive deterioration and is the most common type of dementia. The pathological process consists principally of neuronal loss or atrophy, together with an inflammatory response to the deposition of amyloid plaques and neurofibrillary tangles. The most frequent type of amyloid in the brains of subjects with Alzheimer's disease is composed primarily of $A\beta$ peptide fibrils, $\beta$-amyloid peptide is a 39-43 amino acid peptide derived by proteolysis from a larger protein known as $\beta$-Amyloid Precursor Protein (APP). Mutations in APP result in familial forms of Alzheimer's disease, in addition to cerebral amyloid angiopathy, and senile dementia, characterized by cerebral deposition of plaques composed of $A\beta$ fibrils and other components. The familial form of Alzheimer's disease represents only approximately 10% of the subject population. Most occurrences of Alzheimer's disease are sporadic cases where APP and $A\beta$ do not possess any mutation. The structure and sequence of $A\beta$ peptides of various lengths are well known in the art. Such peptides can be made according to methods known in the art, or extracted from the brain according to known methods (see, e.g., Glenner and Wong, Biochem. Biophys. Res. Comm. 122:1131-35, 1984; Glenner and Wong, Biochem. Biophys. Res. Comm. 129:885-90, 1984). In addition, various forms of the peptides are commercially available.

Alzheimer's disease predisposing factors identified or proposed in the scientific literature include, inter alia, age (e.g., being over 40 years old, such as over 50 years old, over 60 years old, over 70 years old, over 80 years old, over 85 years old, over 90 years old, or over 95 years old), certain genotypes (e.g., presenilin-1, presenilin-2 and APP missense mutations associated with familial AD; α-2-macroglobulin and LRP-I genotypes associated with late-onset AD), environmental factors (e.g., exposure to aluminum), past history of infection by specific viral and bacterial agents (e.g., herpes simplex virus and Chlamydia pneumoniae), and certain vascular factors (e.g., hypertension and diabetes). In a further embodiment, a human subject is shown to be at risk for Alzheimer's disease by a cognitive test such as Clinical Dementia Rating (CDR), Alzheimer's Disease Assessment Scale-Cognition (ADAS-Cog), Disability Assessment for Dementia (DAD), or Mini-Mental State Examination (MMSE). The subject may exhibit a below average score on a cognitive test, as compared to a historical control of similar age and educational background. The subject may also exhibit a reduction in score as compared to previous scores of the subject on the same or similar cognition tests.

In determining the CDR, a subject is typically assessed and rated in each of six cognitive and behavioral categories: (1) memory, (2) orientation, (3) judgment and problem solving, (4) community affairs, (5) home and hobbies, and (6) personal care. The assessment may include historical information provided by the subject or a corroborator who knows the subject well. The subject is assessed and rated in each of these areas and the overall rating, (0, 0.5, 1, 2, or 3) determined. A rating of 0 is considered normal. A subject with a CDR of 0.5 is characterized by mild consistent forgetfulness, partial recollection of events and "benign" forgetfulness, while ratings of 1, 2 and 3 correspond to mild, moderate and severe dementia, respectively. See, for example, Morris, Neurology 43:2412-14, 1993.

Another means to evaluate cognition, particularly in a subject suspected of having Alzheimer's disease, is the ADAS-Cog, or a variation termed the Standardized Alzheimer's Disease Assessment Scale (SADAS). Both tests are commonly used as an efficacy measure in clinical drug trials of Alzheimer's disease and related disorders characterized by cognitive decline. While ADAS-Cog and SADAS were not designed to diagnose Alzheimer's disease per se, they are useful in characterizing symptoms of dementia and are relatively sensitive indicators of dementia progression. See, for example, Doraiswamy, Neurology 48: 1511-17, 1997. The ADAS-cog is designed to measure, with the use of questionnaires, the progression and the severity of cognitive decline as seen in Alzheimer's disease on a 70-point scale. The ADAS-cog scale quantifies the number of wrong answers; consequently, a high score on the scale indicates a more severe case of cognitive decline. Annual deterioration in untreated Alzheimer's disease patients is approximately 8 points per year. See, for example, Raskind, J. Clin. Psychiatry 2:134-38, 2000. The DAD scale has been developed to measure a subject's ability to perform the activities of daily living, and may be assessed according to self care (i.e., dressing and personal hygiene) and instrumental activities (e.g., housework, cooking and using household devices). The objectives of the DAD scale include quantitatively measuring functional abilities in activities of daily living in subjects with cognitive impairments and to help delineate areas of cognitive deficits that may impair performance in activities of daily living. The DAD is administered through an interview with the caregiver. It measures actual performance in activities of daily living of the subject as observed over a two week period prior to the interview. The scale assesses the following domains of activities: hygiene, dressing, telephoning, continence, eating, meal preparation, outing activities, finance and correspondence, medication use, leisure and housework. A total score is obtained by adding the rating for each question; higher scores represent less disability, while lower scores indicate more dysfunction. See, for example, Gelinas et al., Am. J. Occ. Ther. 53:471-81, 1999. The MMSE is a means to evaluate the onset of dementia and the presence of global intellectual deterioration, as seen in Alzheimer's disease and multi-infarct dementia. The MMSE is scored from 1 to 30. The MMSE does not evaluate basic cognitive potential, as, for example, does the so-called "IQ test," but rather tests intellectual skills. A person of "normal" intellectual capabilities will score a 30 on the MMSE objective test. Scores progressively lower than 30 correspond to very mild, mild, moderate, and severe dementia, respectively. See, for example, Folstein, J. Psychiatr. Res. 12:189-98, 1975.

In another embodiment of the disclosure, the subject is a human, for example, a human at risk for Parkinson's disease. Parkinson's disease is a neurodegenerative disease characterized by muscle rigidity, tremor, a slowing of physical movement (bradykinesia), and in extreme cases, a loss of physical movement (akinesia). The primary symptoms are the results of decreased stimulation of the motor cortex by the basal ganglia, normally caused by the loss of pigmented dopamine-secreting (dopaminergic) cells. The mechanism by which the brain cells in Parkinson's disease are lost includes an abnormal accumulation of the protein α-synuclein bound to ubiquitin in the damaged cells. Without being bound by theory, it is believed that the α-synuclein-ubiquitin complex cannot be directed to the proteosome, due to a defect in the machinery that transports proteins between the endoplasmic reticulum and the Golgi apparatus. This protein accumulation forms proteinaceous cytoplasmic inclusions called Lewy bodies.

The Unified Parkinson's Disease Rating Scale (UPDRS) is the primary clinical tool used to assist in diagnosis and determine severity of PD, and includes the following sections: (1)(Mentation, behavior, and mood; (2) Activities of daily living; (3) Motor examination; (4) Complications of therapy; (5) Modified Hoehn and Yahr Staging; and (6) Schwab and England Activities of Daily Living Scale. See, for example, Fahn S., Marsden C D., Calne D. B., and Goldstein M., eds. Recent Developments in Parkinson's Disease, Vol 2. Macmillan Health Care Information, Florham Park, N.J., 1987, pp 153-63; 293-304.

Methods of identifying compounds that inhibit aggregation-mediated proteotoxicity in a subject are also disclosed herein. Any compound that has the ability (whether or not ultimately realized) to: (1) prevent or inhibit amyloid protein assembly into insoluble fibrils; (2) facilitate clearance of preformed amyloid deposits; (3) slow amyloid deposition in subjects already having amyloid deposits; (4) prevent amyloid protein (soluble and/or fibrillar) from binding or adhering to a cell surface; or (5) block amyloid-induced cellular toxicity is contemplated for use in the methods of the disclosure.

It is further to be understood that all base sizes or amino acid sizes, and all molecular weight or molecular mass values, given for nucleic acids or polypeptides are approximate, and are provided for description. The following examples are offered by way of illustration and not by way of limitation.

Examples

Example 1

Identifying Compounds That Inhibit Aggregation-Mediated Proteotoxicity

Figure 2:
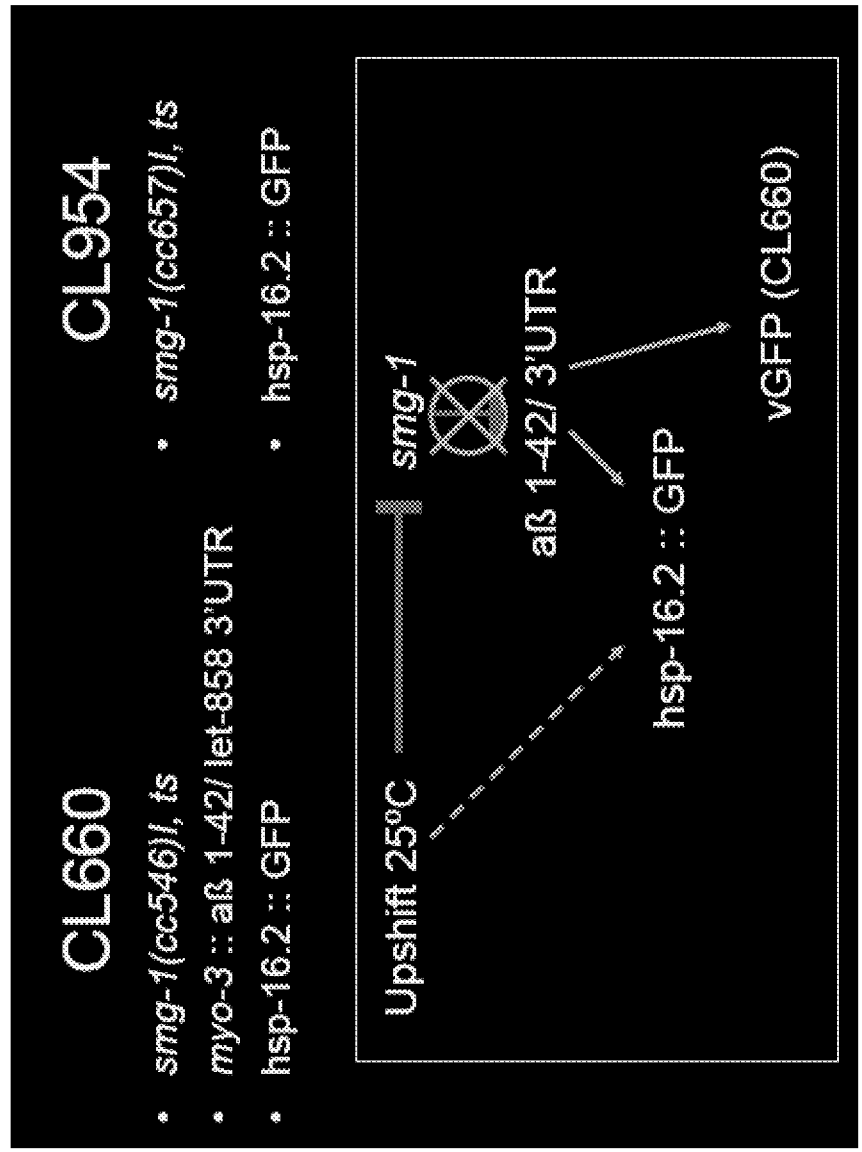
FIG. 2 shows a schematic of the transgenic C. elegans model of aggregation described herein.
Figure 3:
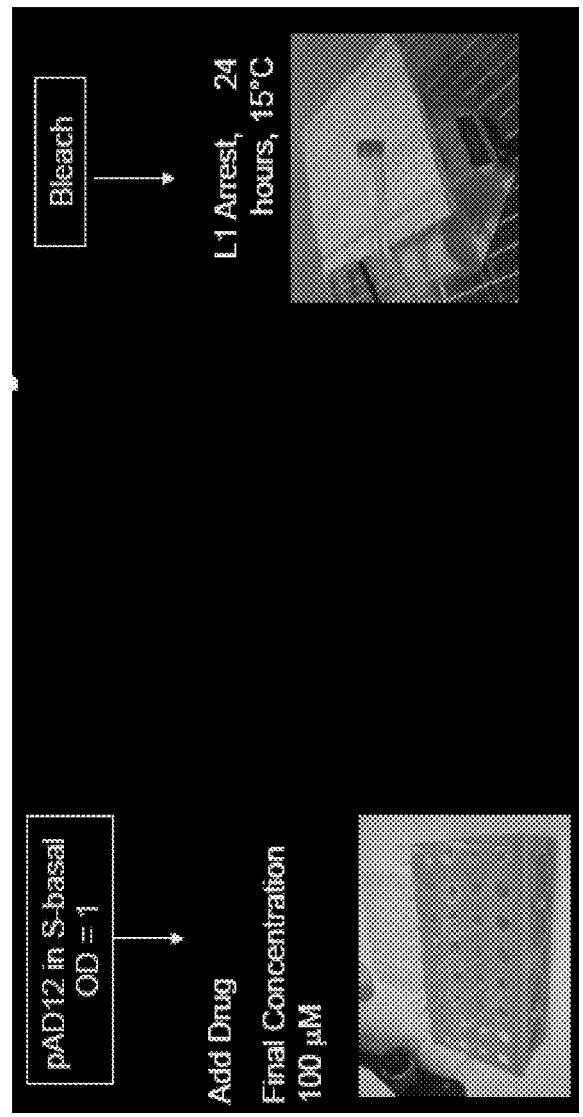
FIGS. 3, 4 and 5 show an exemplary assay of the disclosure.
Figure 4:
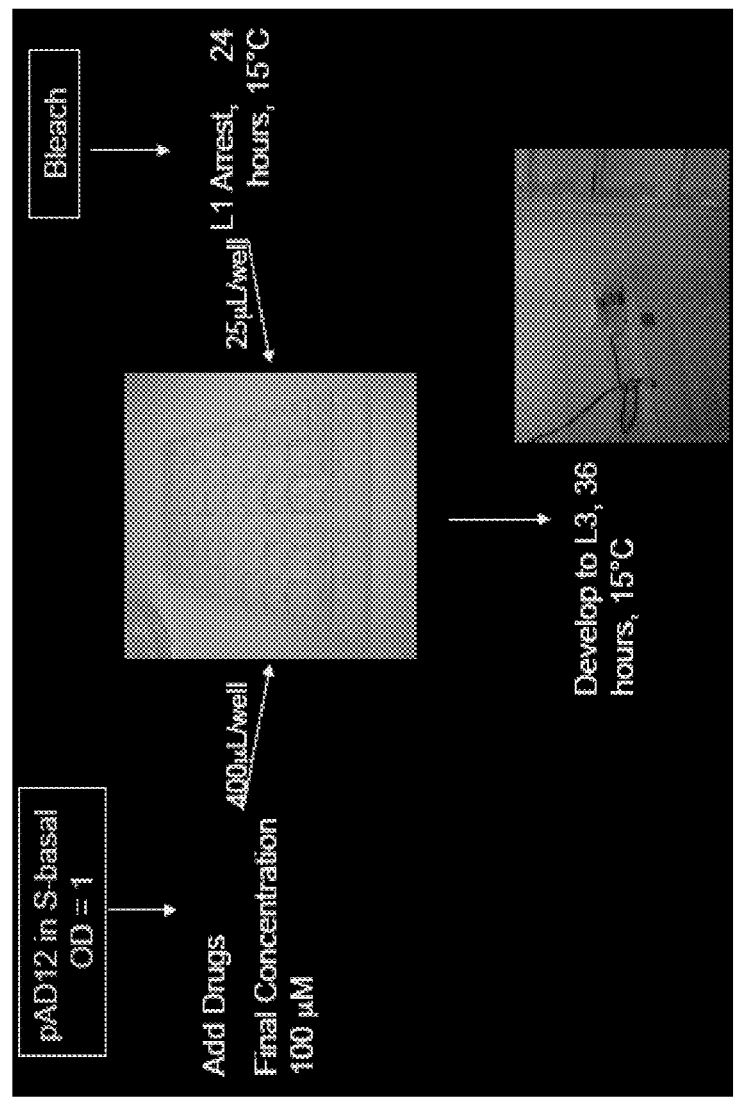
Figure 5:
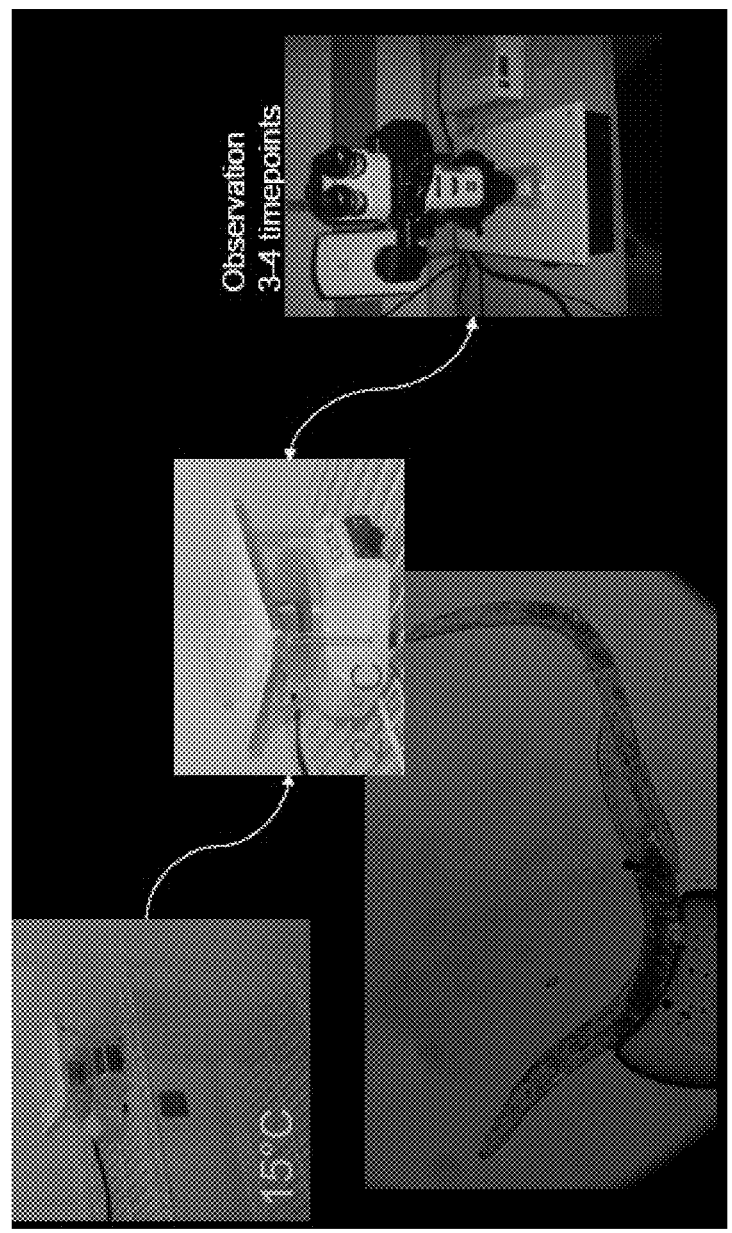
Figure 6:
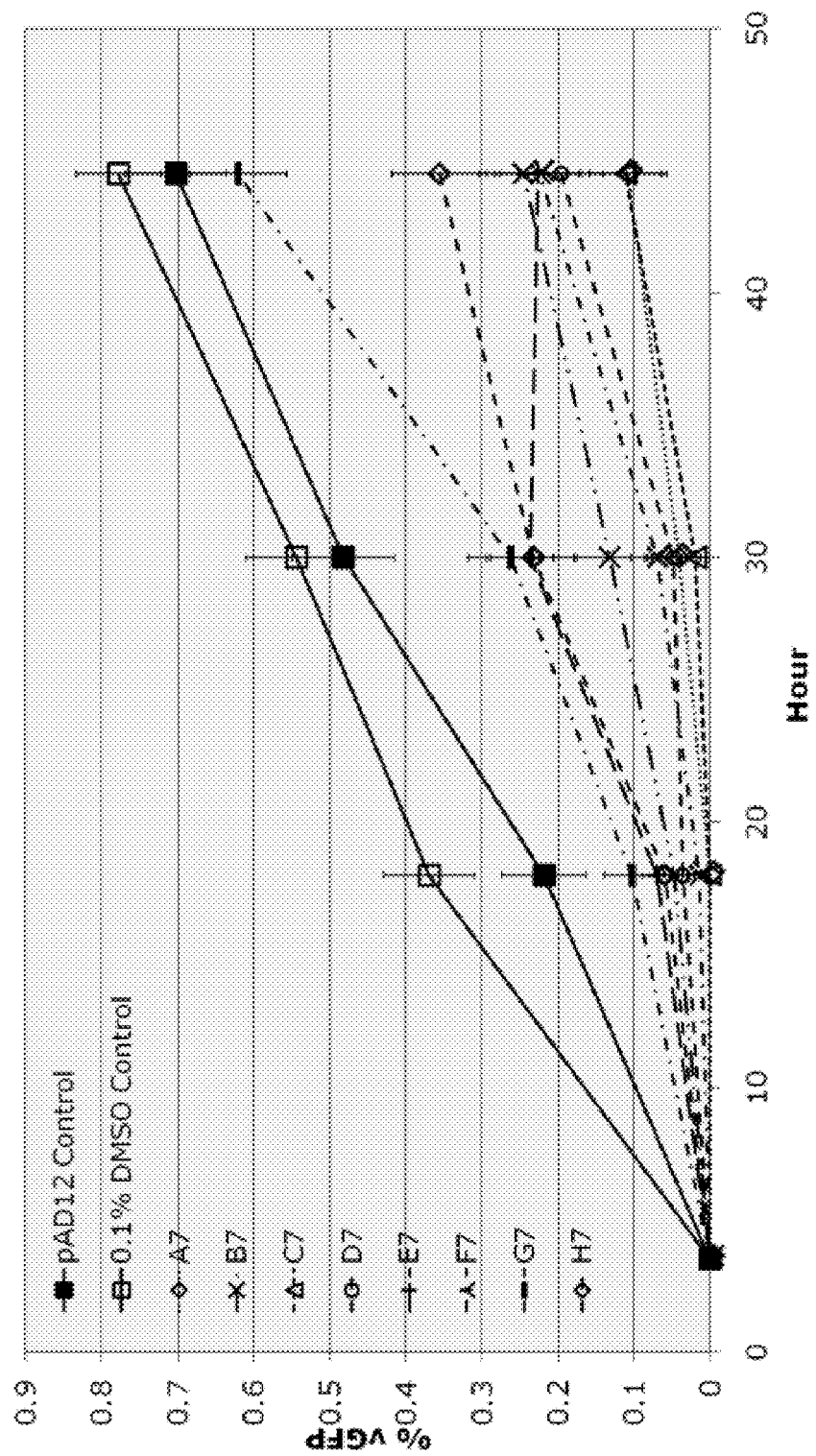
FIGS. 6-9 show the effects on fluorescence of certain agents of the disclosure.
Figure 7:
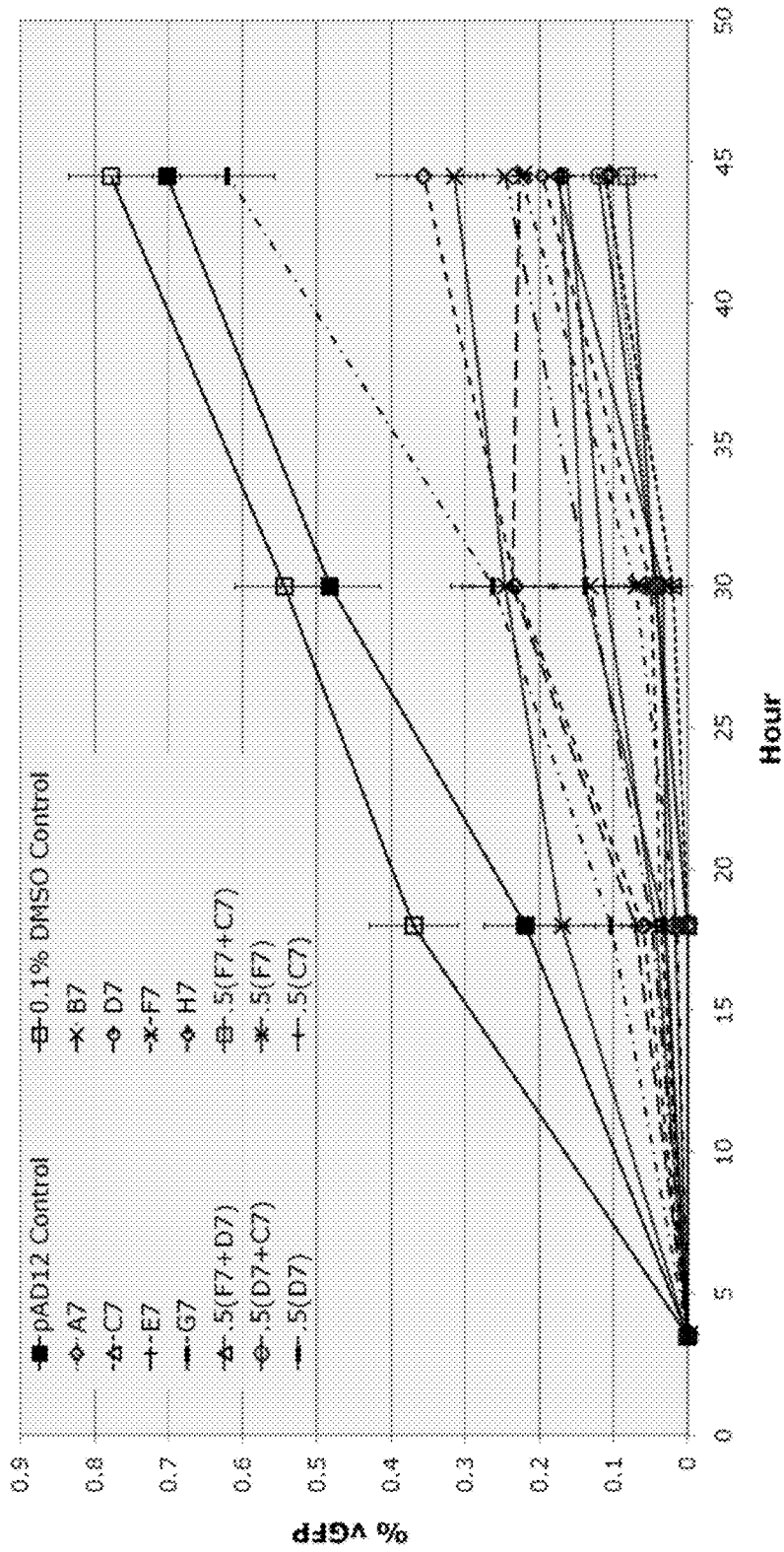
Figure 8:
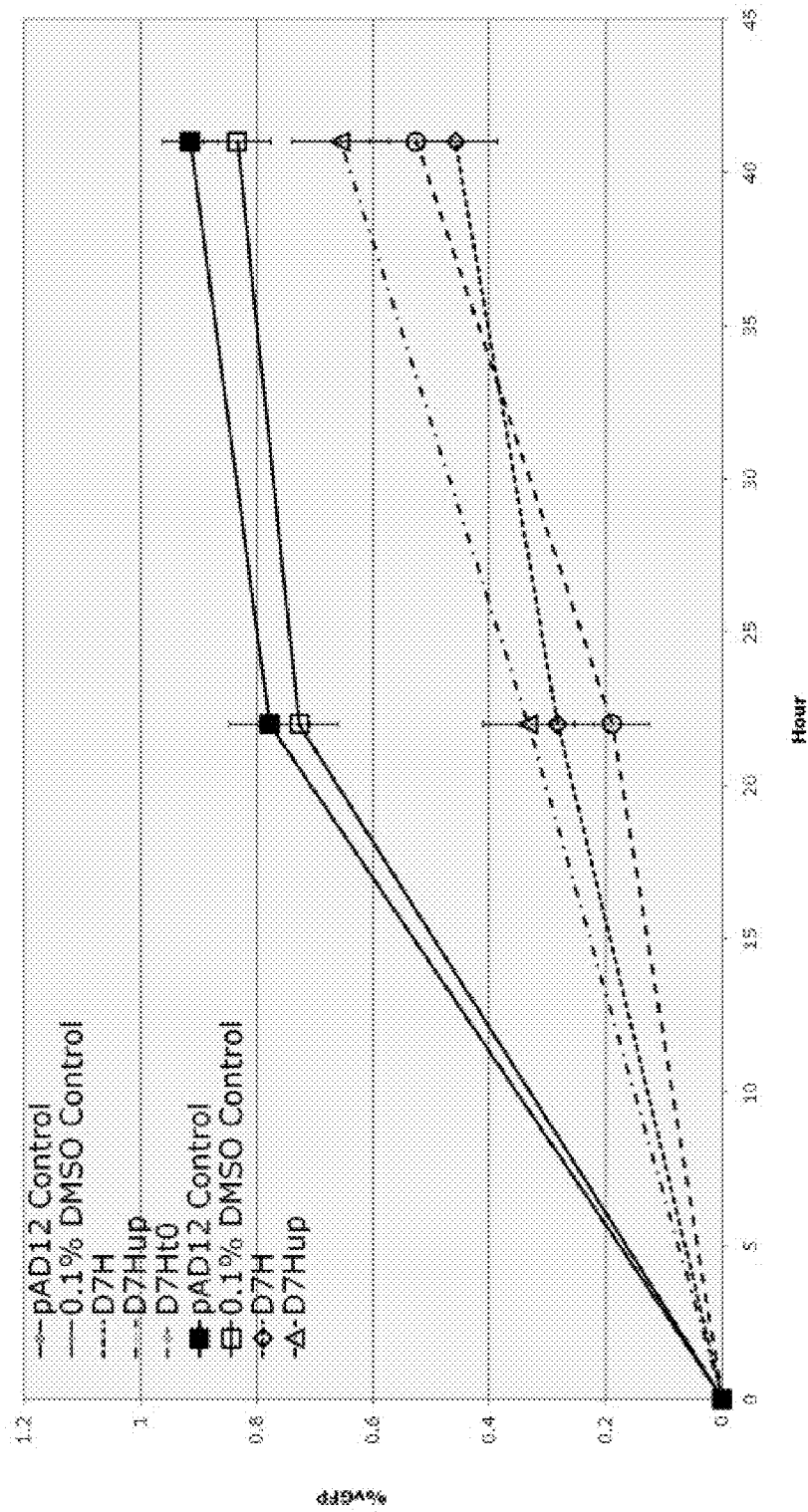
Figure 9:
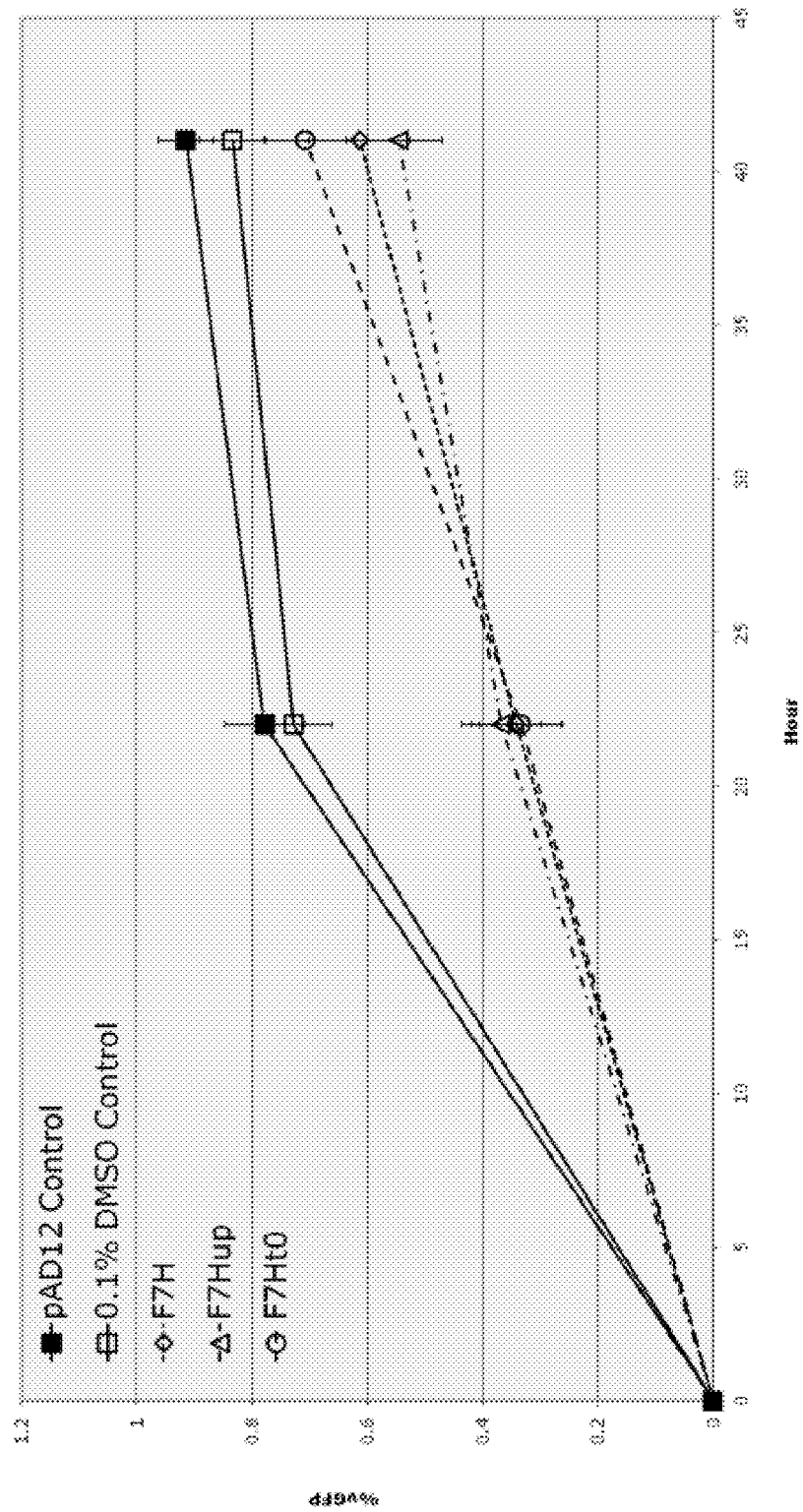
Figure 10:
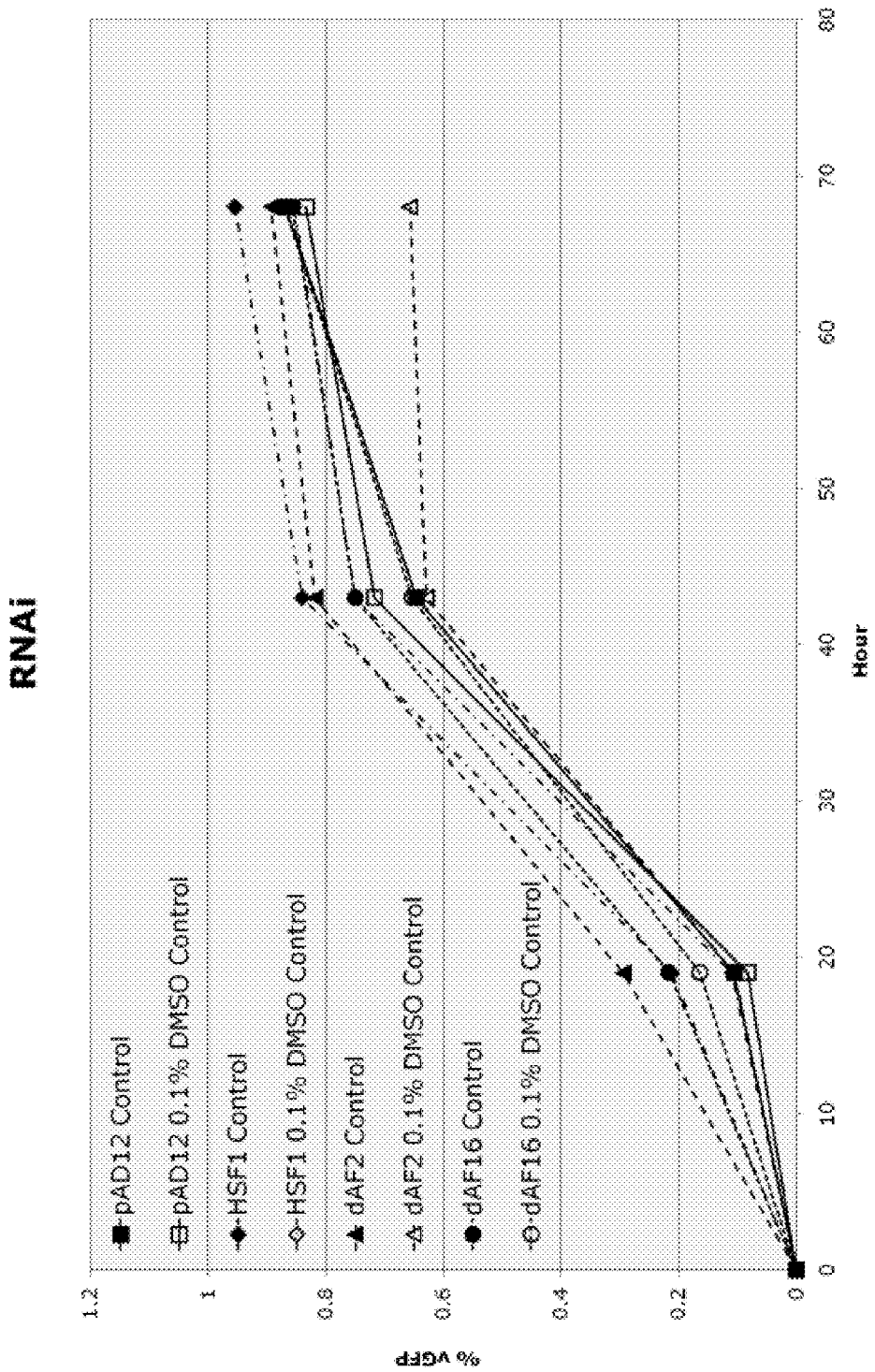
FIGS. 10 and 11 show RNAi assays using RNAi against HSF1, dAF2 and dAF16.
Figure 11:
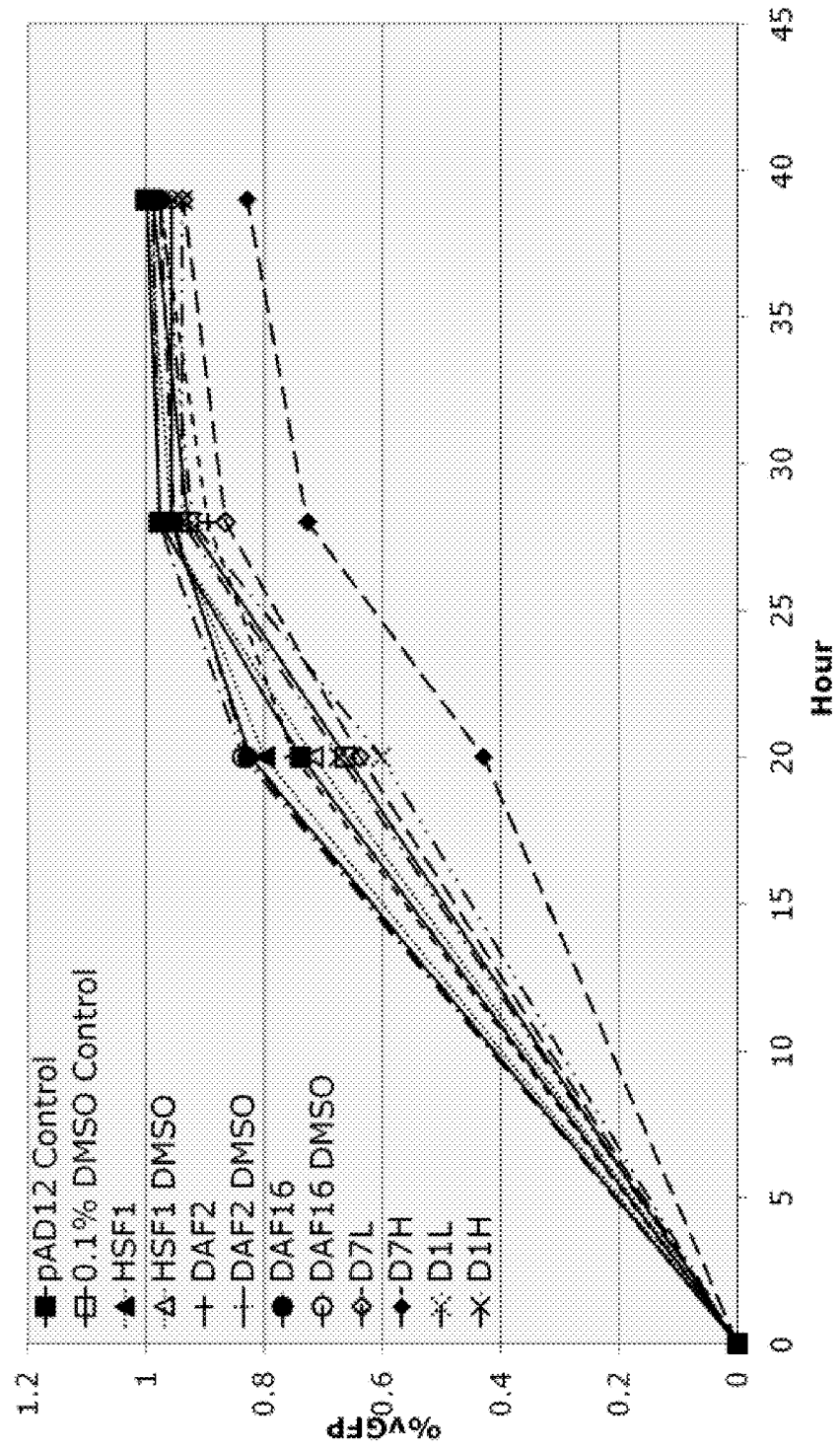
Figure 12:
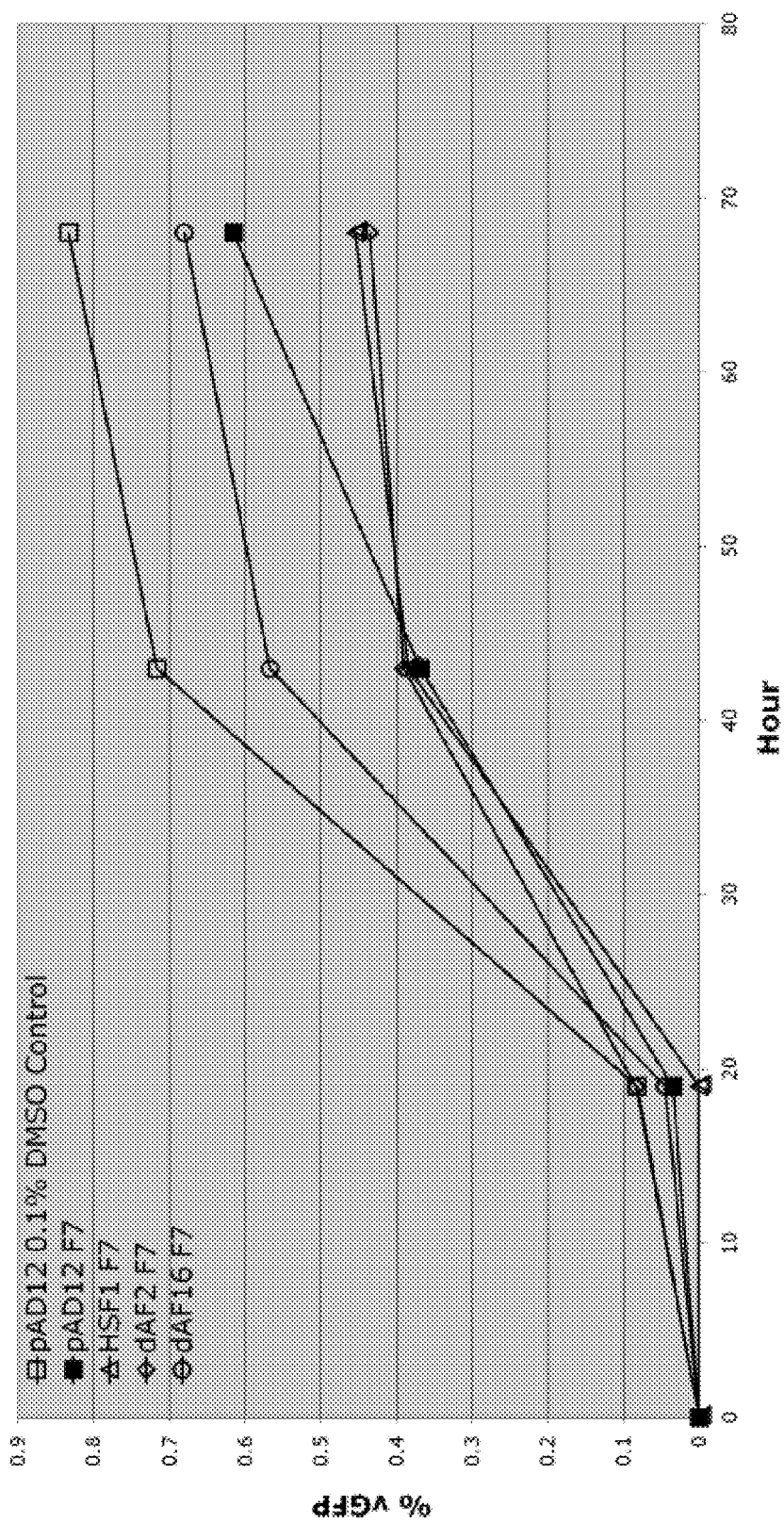
FIGS. 12 and 13 shows the effect of a combination of agent (FIG. 12.) F7 and (FIG. 13) D7, in the presence of RNAi.
Figure 13:
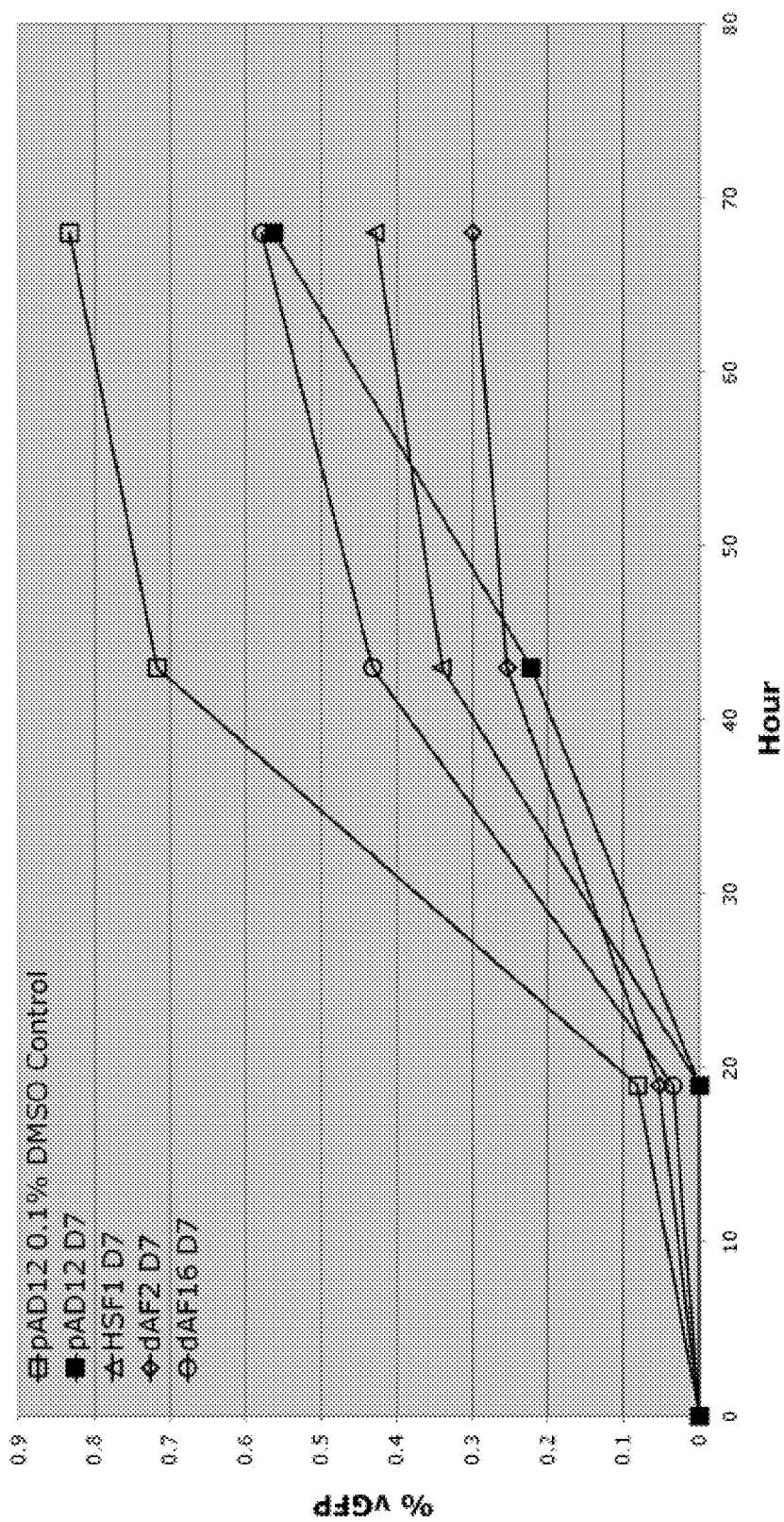
Figure 14:
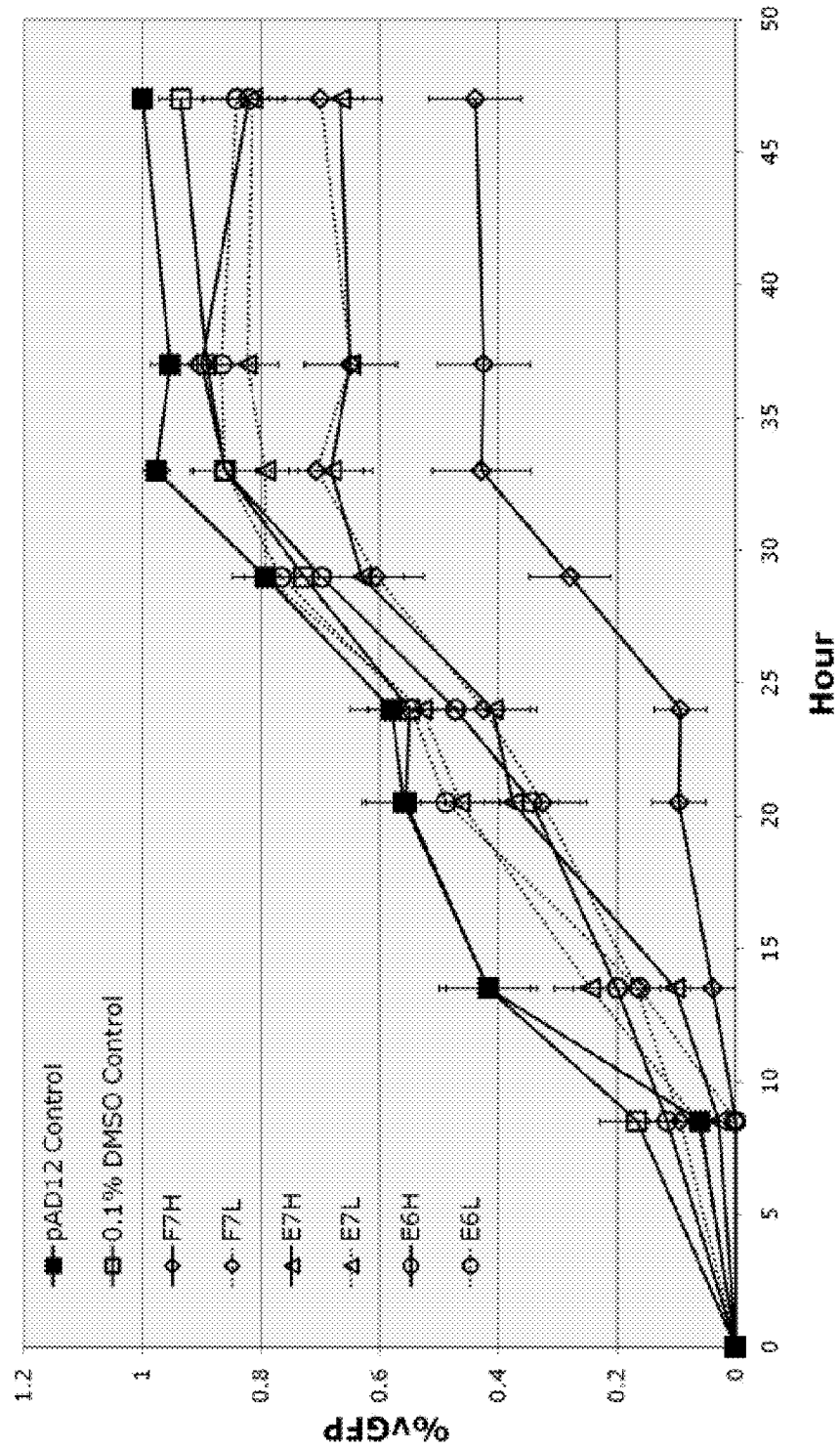
FIG. 14 shows results for agents E6, E7 and F7 (H, high, L, Low).
Figure 15:
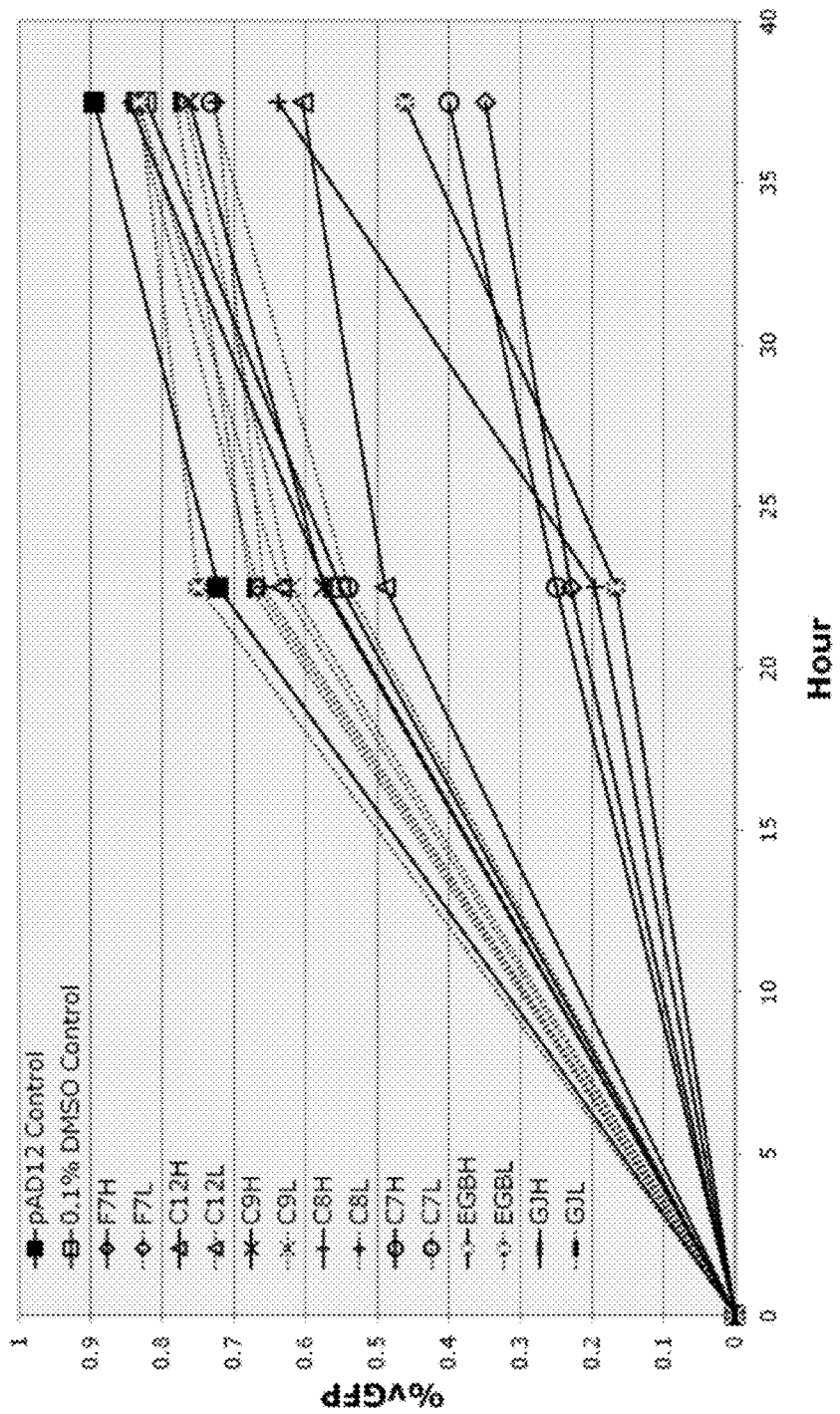
FIG. 15 shows the effect of certain agents (e.g., F7, C12, C9, C8, C7) at either High (H) or Low (L) concentrations in the worm model of protein aggregation.
Figure 16:
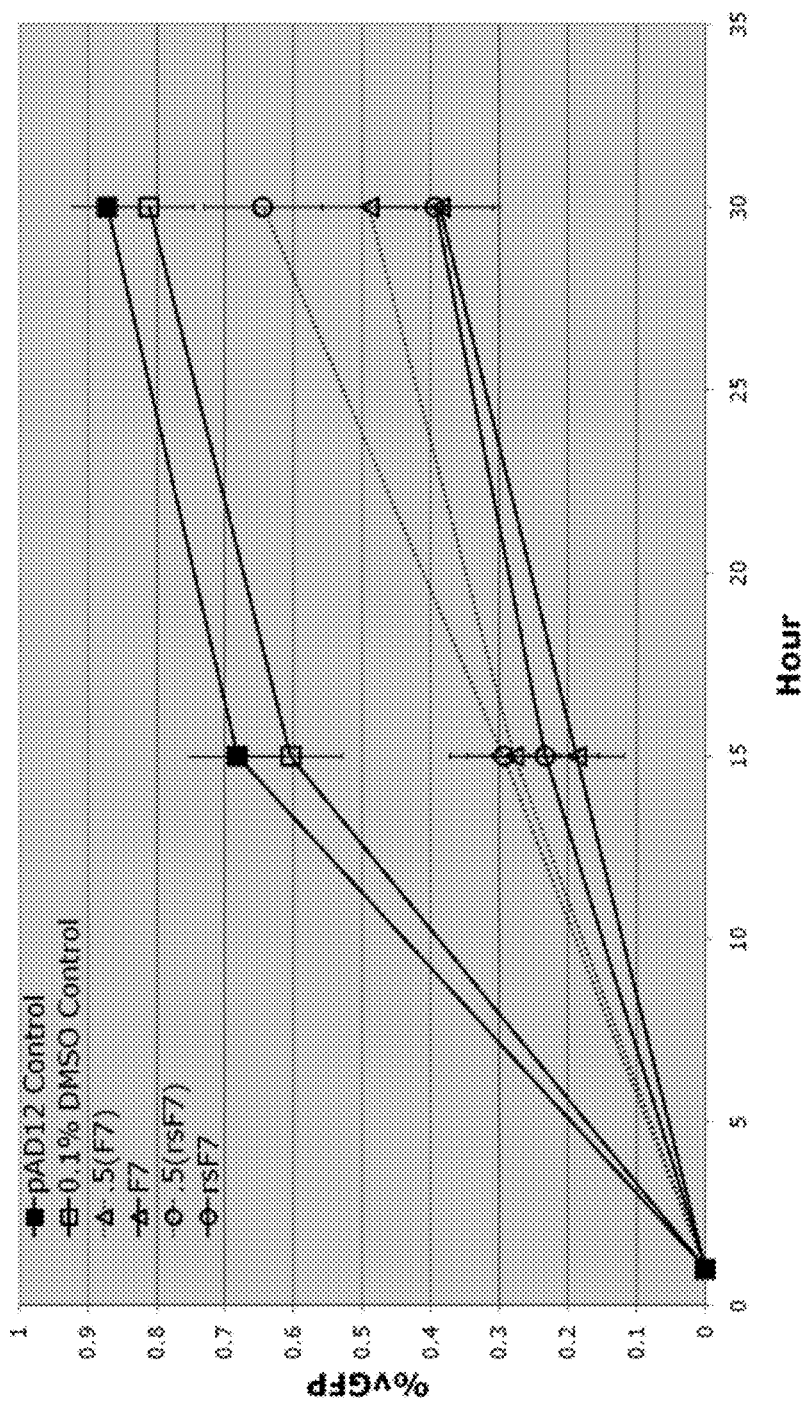
FIG. 16 shows the effect of resynthesized compound F7 in the assay of protein aggregation in the C. elegans model described in the Example.
Figure 17:
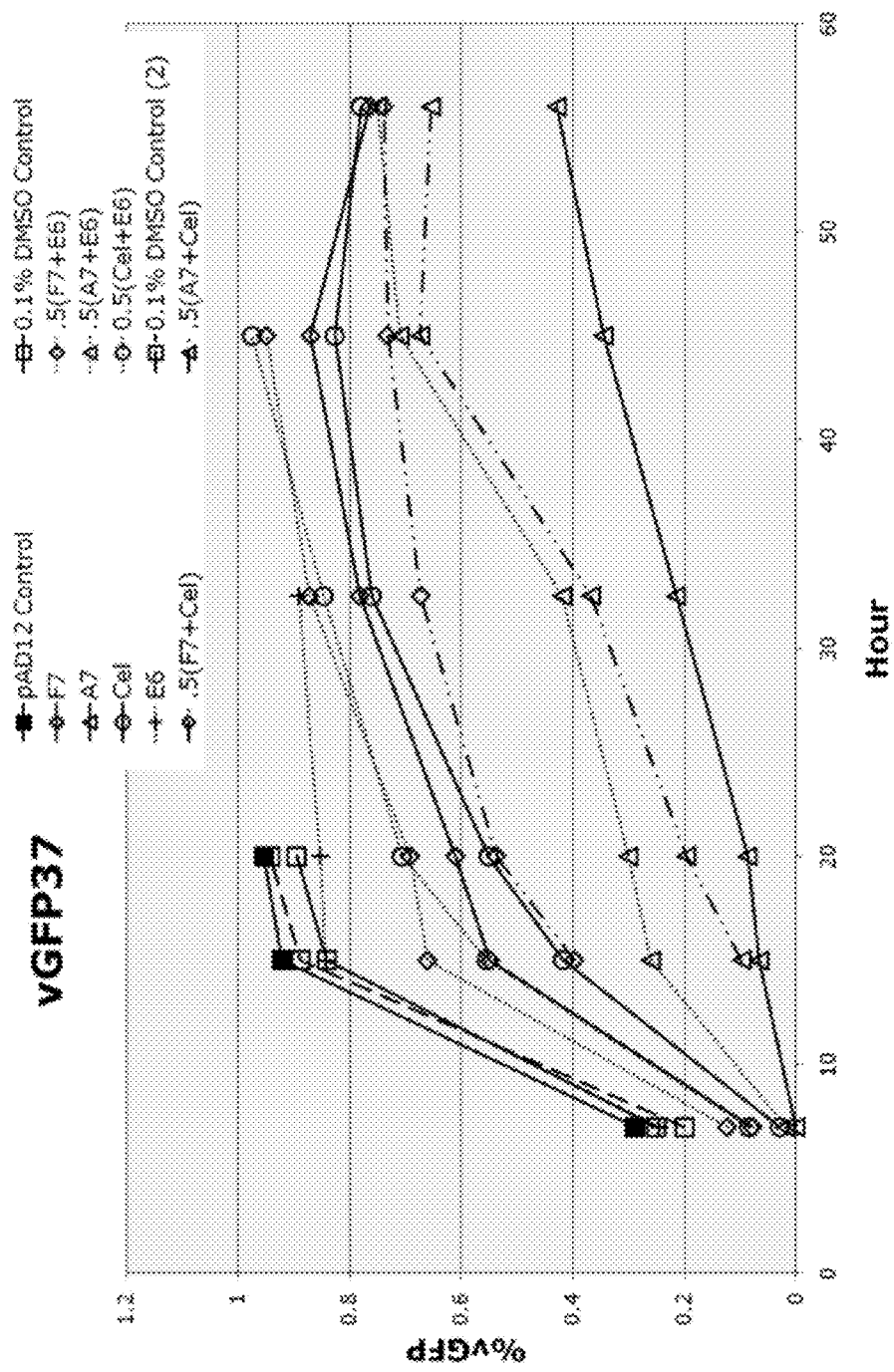
FIG. 17 shows the effect of combinations of agents on the assay protein aggregation in the C. elegans model described in the Example.

Identification of compounds that inhibit aggregation-mediated proteotoxicity was carried out using transgenic *C. elegans* strain, which expresses human Aβ1-42 within body wall muscles under the direction of the myo-3 promoter cause by induction at 25 C and inhibition of smg-1 activity. This induction in the absence of an effective inhibitor causes association of a heat shock protein-GFP fusion construct with the Aβ1-42 (a schematic of this model is shown in FIG. 2).

Bleaching and Plating.

*C. elegans* (transgenic strain) were decontaminated and disrupted using bleach. After the final rinse of M-9 solution (42 mM $Na_2HPO_4$, 22 mM $KH_2PO_4$, 86 mM NaCl, 1 mM $MgSO_4$) the unhatched eggs were left in about 10 ml of M-9 solution to time-sync the growth of the nematodes. If an unusually high concentration of eggs were present, then they were split into two conical tubes, each having 10 ml total M-9 solution. The tube(s) was placed on a rocker in a 15° C. fridge. Twenty-four hours after placing on the rocker, the conical tubes were removed from the fridge, and inspected under a microscope for hatched worms. A centrifuge was used to pellet the worms, and all but 3 ml of the M-9 solution was removed; the worms were resuspended by shaking the tube a couple of times.

Worms were spotted onto primary plates (previously spotted with *E. coli* OP50) in 50 μl aliquots, taking care that the plates remained flat and that the entire worm aliquot landed within the spot of OP50 already on the plates. Once the worms reached the L1 stage, the plates were placed into the 15 C fridge, again taking care to keep the plates flat.

Fileting.

Twenty-four hours after placing the L1-stage worms into the fridge, the plates were removed for fileting. Fifteen to twenty-five worms each were placed into wells of a microtiter plate containing compounds to be tested in an aqueous environment or a corresponding control. Only worms that were moving normally were filleted. The worms were incubated for approximately 36 hours or until L3 stage was reached. Aβ toxicity was then generated by growing the worms at 25 C for 18 hours which effects smg-1 activity. The worms were observed at 3-4 time points under an optical/fluorescence microscope. Typically the worms settled to the bottom of the well and were counted manually.

Scoring of the worms could also be performed by paralysis analysis. When paralysis of a worm was suspected, a pick was used for probing. When no muscle contractions behind the neck were observed, the worm was removed from the spot of OP50 and placed onto an area of clean agar for additional probing. If there was still no muscle contraction behind the neck, the worm was scored as "paralyzed," removed from the plate and flamed. Any worms that exhibited muscle contractions were scored as "alive."

Example 2

Animals were grown at 15° C. until adulthood. Gravid adults were suspended and bleached; eggs were resuspended in M9 salt solution and allowed to hatch for 24 hours at 15° C. Compounds were added to S-media at 100 μM concentration and then aliquoted to 48-well Costar plates at 400 μL per well. As a control, DMSO was added to S-media at 0.1% concentration. L1 hatched larvae were added to each well at 50-100 animals per 25 μL aliquot. Worms were thus grown in liquid media until reaching the third larval stage (L3) at 15° C. At L3 worms were shifted to 25° C. to begin biogenesis of Aβ protein. Observation began 24 hours later when the animals have reached adulthood (timepoint=0 hrs). Animals were scored as either with or without vGFP signal, regardless of intensity level.

Compounds were synthesized as variations on chemical structure of flavones and categorized in 96-well libraries so that both columns and rows contain related chemical structure. Enantiomers of hits were synthesized and tested the same as described above.

Figure 18:
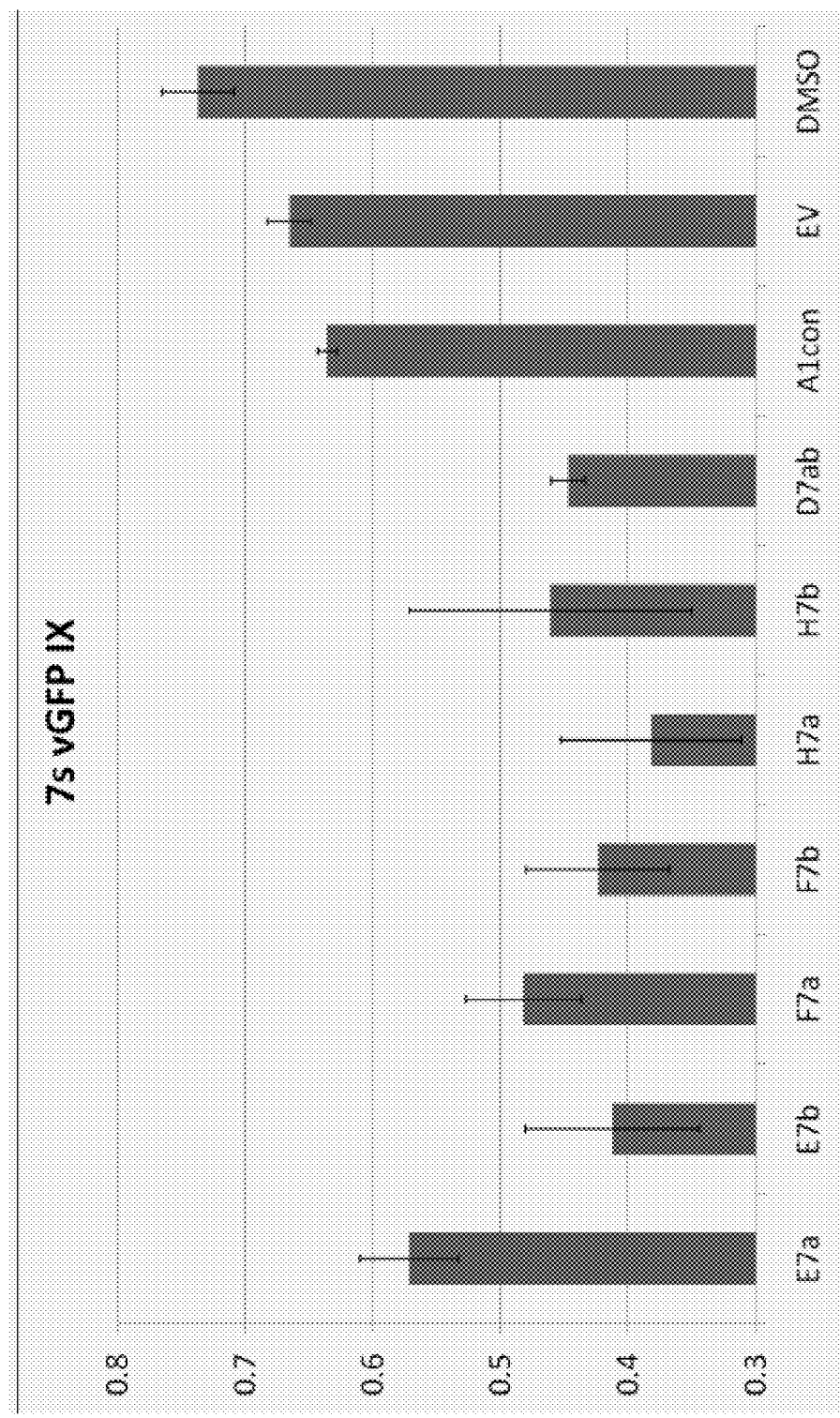
FIG. 18 shows a graph of the effect of diketopiperazines (E7, F7, H7 and D7). The diketopiperazines show reduced vGFP in CL660 animals when compared to control experiments. Data shown is 36 hours into adulthood. Error bars are standard deviations of 3 experiments; n=100.

Out of the compounds tested within a 96-well library of synthetic compounds, a group of compounds was able to reduce vGFP expression in CL660 animals. A family of diketopiperazines (DKPs) (e.g. having the general formula I or II) reduced vGFP levels significantly below levels of control groups (FIG. 18). These data suggest that these compounds have a protective role against the buildup of Aβ protein in the vulval muscle cells of the animals.

In order to determine a pathway the compounds are acting upon, experiments were performed with genetics already known to be involved in the handling of Aβ aggregation. The insulin/IGF-1 pathway plays a role in the handling of cellular stress. DAF-2 is the sole insulin/IGF-1 receptor in *C. elegans* and depletion of DAF-2 results in long-lived, stress resistant worms. The Aβ protein applies a biochemical stress to cellular activity as shown by the hsp-16.2 activity in response to its presence. Two downstream targets of DAF-2, DAF-16 and HSF-1, have been shown to regulate either aggregative or disaggregative activity, respectively, to handle the load of toxic Aβ protein. DAF-16 encodes a FOXO transcription factor and is required for the lifepan extension in worms fed daf-2RNAi. HSF-1 is also required for the lifespan extension seen in worms fed daf-2 RNAi.

Figure 19:
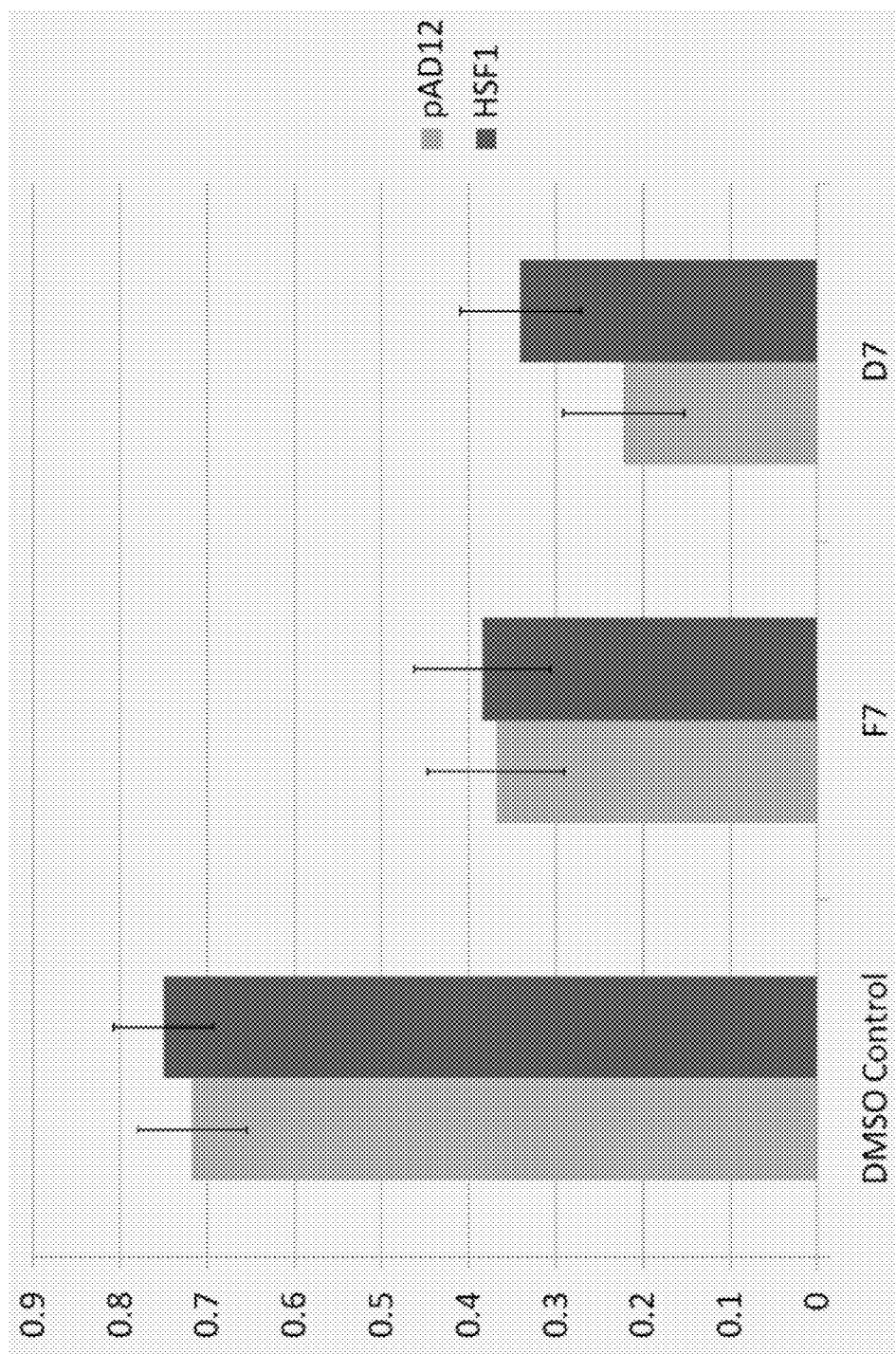
FIGS. 19 and 20 shows daf-16 RNAi dampens the beneficial effects seen by DKPs in CL660 animals (FIG. 19), unlike hsf-1 RNAi (FIG. 20).
Figure 20:
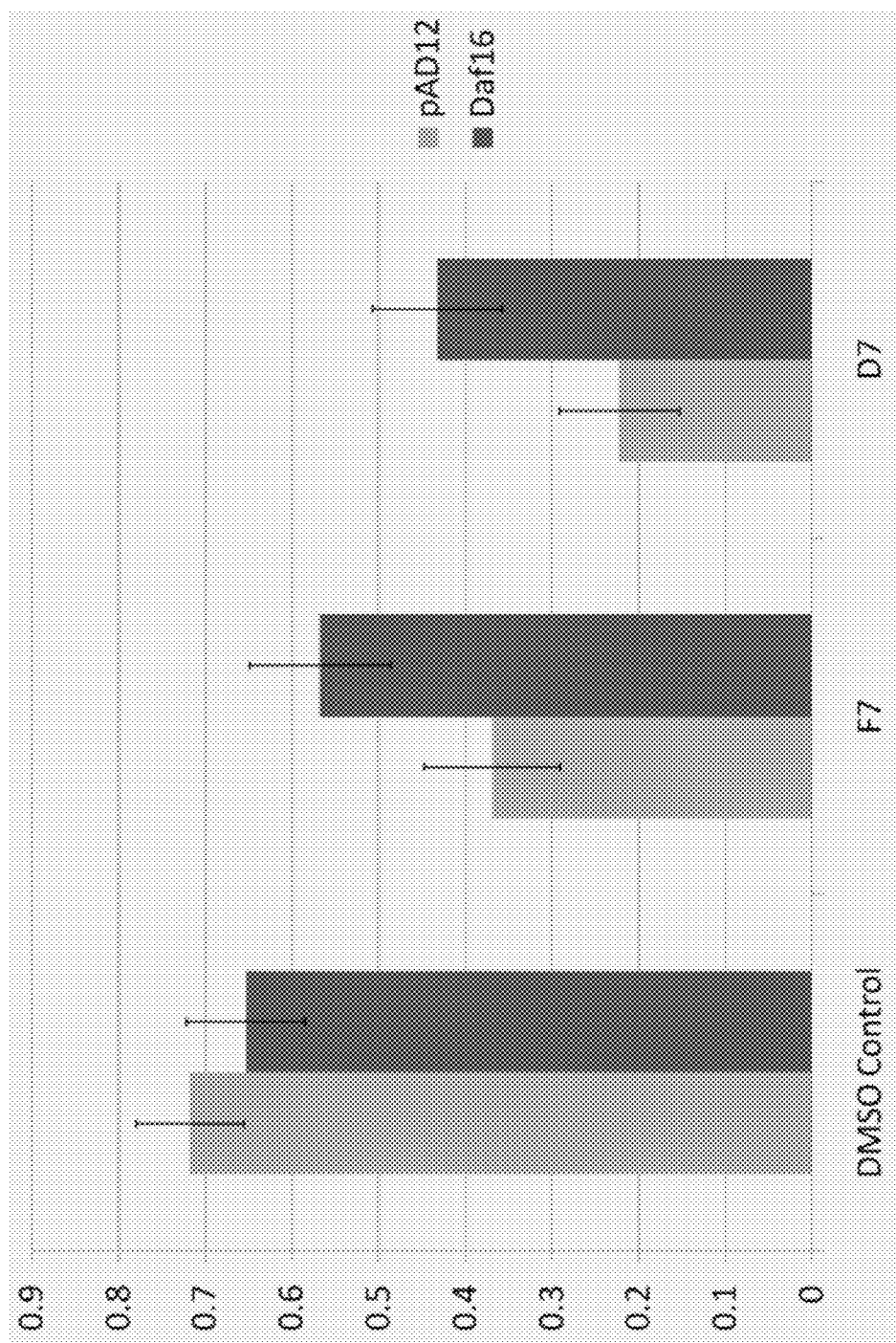

CL660 animals were fed bacteria expressing RNAi suspended in S-basal solution. Knockdown of DAF-16 in worms partially suppressed the beneficial effects of F7 and D7 from the DKP family (FIG. 19), whereas knockdown of HSF-1 had no effect on vGFP expression (FIG. 20). These data suggest that DKPs are acting on the aggregative pathway DAF-16, but not on the disaggregative pathway HSF-1.

Figure 21:
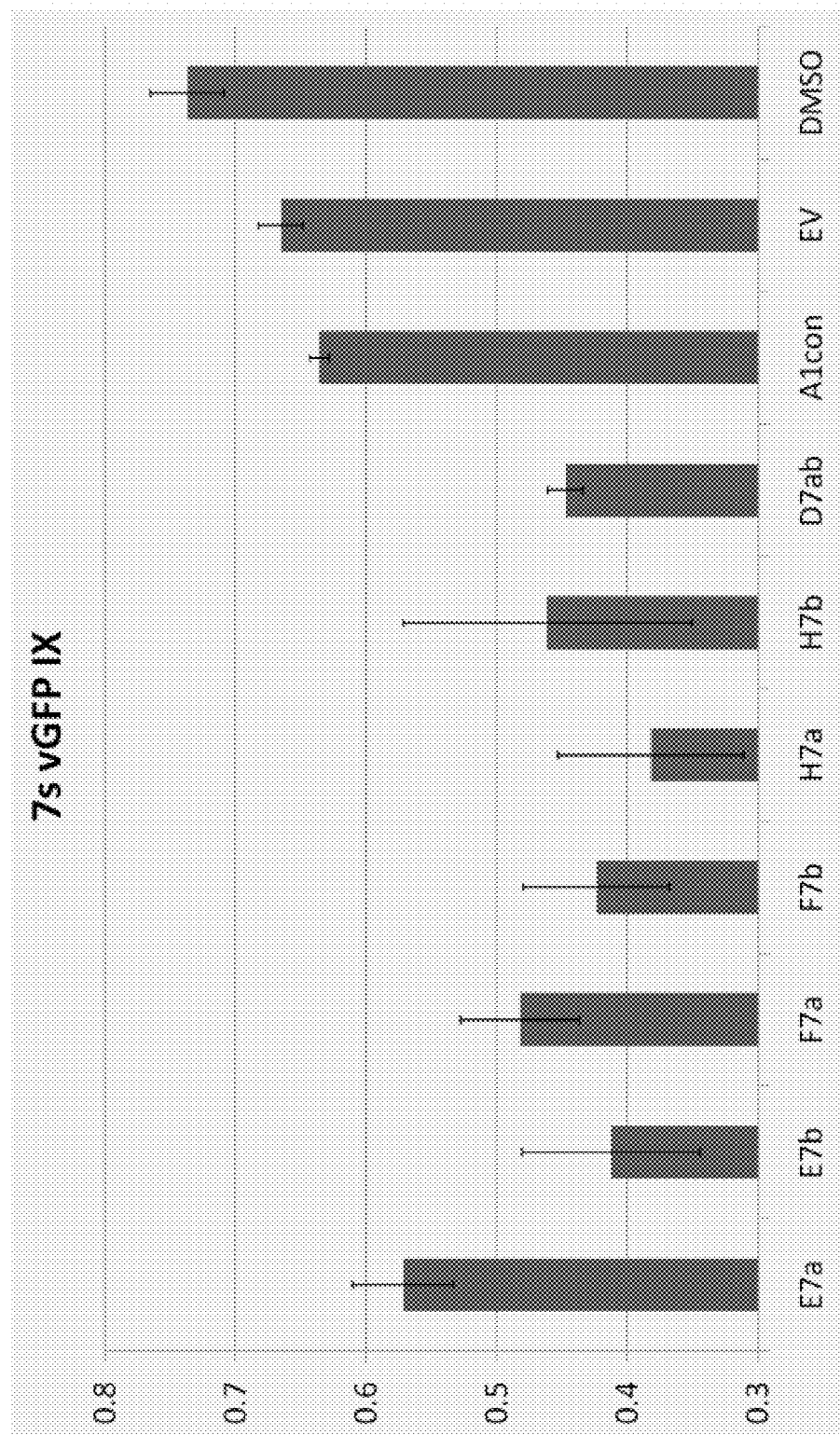
FIG. 21 show enantiomers of diketopiperazines also reduce vGFP in CL660 animals.

Enantiomers of each of the above tested compounds to investigate if one stereoisomer would work better or the same as the other. With the exception of one stereoisomer, each compound significantly reduced vGFP signaling below that of controls (FIG. 21). The exception (E7a) has moderately reduced signaling. These data suggest that both stereoisomers are able to significantly reduce Aβ toxicity.

Although the foregoing disclosure has been described in some detail by way of illustration and example for purposes of clarity of understanding, it will be obvious that certain changes and modifications may be practiced within the scope of the appended claims.

What is claimed:

1. A compound having the general formula I:

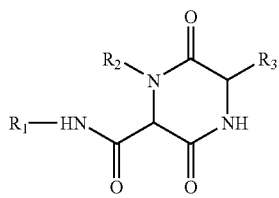

(I)

wherein:
$R_1$ is aryl, heteroaryl, arylalkyl, or heteroarylalkyl, each optionally substituted;
$R_2$ is alkyl, substituted alkyl, aryl, substituted aryl, heteroaryl or substituted heteroaryl;
$R_3$ has a formula selected from the group consisting of —$R_4$—X—$R_5$ and —$C(R)_2$—$C(R)_2$—$C(R)_2$—$R_6$;
$R_4$ is a bond, alkyl, substituted alkyl, aryl or substituted aryl;
$R_5$ is H, alkyl, substituted alkyl, aryl, substituted aryl, or an alcohol protecting group;
X is selected from the group consisting of O, S, N(R), C(O), C(O)NR, $S(O)_n$, wherein n is 0, 1 or 2;
$R_6$ is selected from the group consisting of aryl, optionally substituted aryl, heteroaryl, and substituted heteroaryl; and
each R is independently selected from the group consisting of H, aryl, substituted aryl, alkyl, or substituted alkyl; and a salt thereof.

2. The compound of claim 1, wherein $R_1$ is arylalkyl or substituted arylalkyl.

3. The compound of claim 2, wherein $R_1$ is phenylmethyl or substituted phenylmethyl.

4. The compound of claim 2, wherein $R_2$ is alkyl or substituted alkyl.

5. The compound of claim 1, wherein $R_2$ is alkyl or substituted alkyl.

6. The compound of claim 5, wherein $R_2$ is selected from the group consisting of arylalkyl, substituted arylalkyl, heteroarylalkyl and substituted heteroarylalkyl.

7. The compound of claim 6, wherein $R_2$ is phenylmethyl or substituted phenylmethyl.

8. The compound of claim 6, wherein $R_2$ is pyridylmethyl or substituted pyridylmethyl.

9. The compound of claim 5, wherein $R_2$ is alkyl substituted with heterocycle, wherein said alkyl or heterocycle are each optionally substituted.

10. The compound of claim 1, wherein X is O.

11. The compound of claim 5, wherein $R_5$ is an alcohol protecting group selected from the group consisting of an acetyl (Ac), a benzoyl (Bz), a benzyl (Bn), a β-methoxyethoxymethyl ether (MEM), a dimethoxytrityl[bis-(4-methoxyphenyl)phenylmethyl, DMT], a methoxymethyl ether (MOM), a methoxytrityl[(4-methoxyphenyl)diphenylmethyl, MMT), a p-methoxybenzyl ether (PMB), a methylthiomethyl ether, a pivaloyl (Piv), tetrahydropyranyl (THP), a trityl (triphenylmethyl, Tr), a silyl ether, a methyl ether, and an ethoxyethyl ether (EE) protecting group.

12. The compound of claim 1, wherein the compound is:

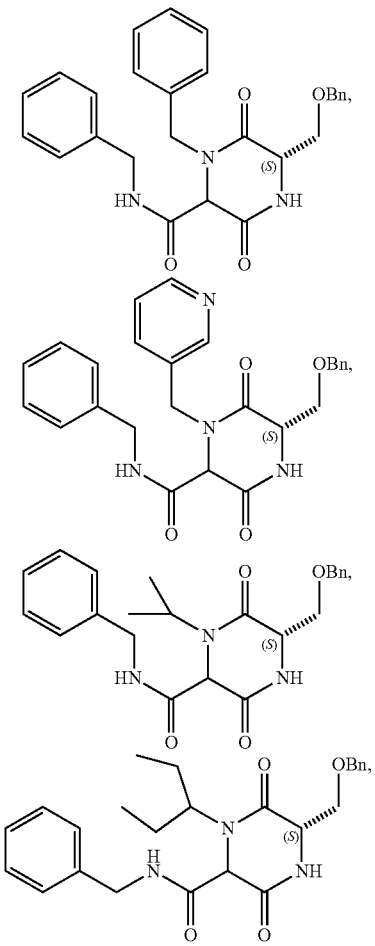

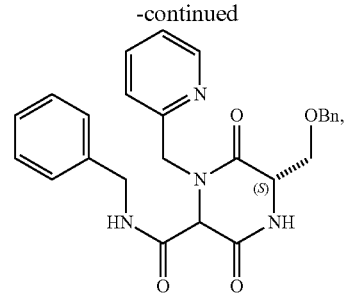

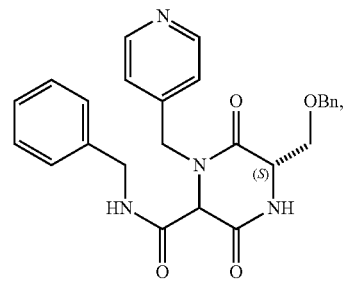

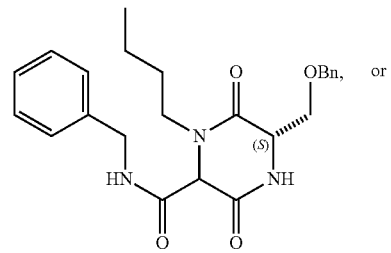

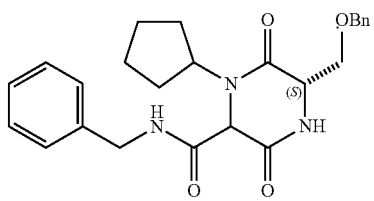

or

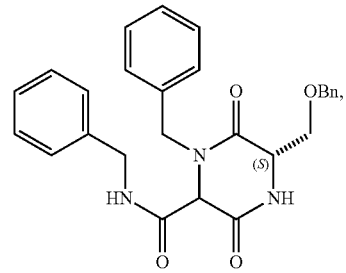

13. The compound of claim 1 in a pharmaceutically acceptable carrier.

14. A method of inhibiting aggregation-mediated proteotoxicity disease consisting of Alzheimer's, Parkinson's, Huntington's and type-2 diabetes diseases in a subject comprising administering to said subject a composition comprising a therapeutically effective amount of a compound of claim 1.

15. The method of claim 14, wherein the compound is:

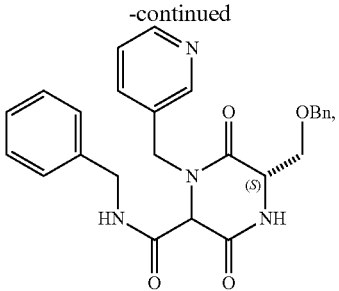

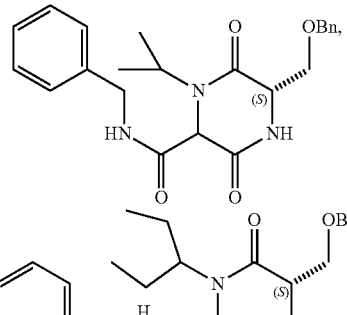

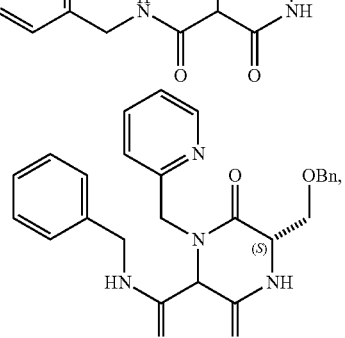

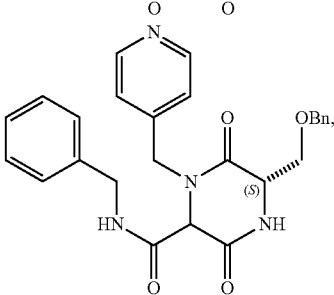

or

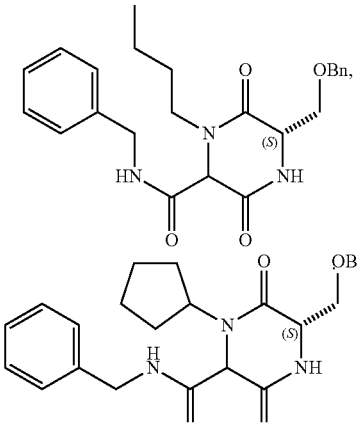

* * * * *